US009417190B2

(12) United States Patent
Hindson et al.

(10) Patent No.: US 9,417,190 B2
(45) Date of Patent: Aug. 16, 2016

(54) CALIBRATIONS AND CONTROLS FOR DROPLET-BASED ASSAYS

(71) Applicant: Bio-Rad Laboratories, Inc., Hercules, CA (US)

(72) Inventors: Benjamin J. Hindson, Livermore, CA (US); Billy W. Colston, Jr., San Ramon, CA (US); Kevin D. Ness, Pleasanton, CA (US); Donald A. Masquelier, Tracy, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 93 days.

(21) Appl. No.: 13/945,661

(22) Filed: Jul. 18, 2013

(65) Prior Publication Data

US 2013/0302792 A1 Nov. 14, 2013

Related U.S. Application Data

(63) Continuation-in-part of application No. 13/251,016, filed on Sep. 30, 2011, now abandoned, and a continuation-in-part of application No. 13/245,575, filed on Sep. 26, 2011, now abandoned, and a continuation-in-part of application No. 12/976,827, filed on Dec. 22, 2010, said application No. 13/245,575 is a continuation of application No. 12/586,626, filed on Sep. 23, 2009, now Pat. No. 9,156,010.

(60) Provisional application No. 61/194,043, filed on Sep. 23, 2008, provisional application No. 61/206,975, filed on Feb. 5, 2009, provisional application No. 61/271,538, filed on Jul. 21, 2009, provisional application No. 61/275,731, filed on Sep. 1, 2009, provisional application No. 61/277,200, filed on Sep. 21, 2009, provisional application No. 61/277,203, filed on Sep. 21, 2009, provisional application No. 61/277,204, filed on Sep. 21, 2009, provisional application No. 61/277,216, filed on Sep. 21, 2009, provisional application No. 61/277,249, filed on Sep. 21, 2009, provisional application No. 61/277,270, filed on Sep. 22, 2009, provisional application No. 61/309,845, filed on Mar. 2, 2010, provisional application No. 61/341,218, filed on Mar. 25, 2010, provisional application No. 61/317,635, filed on Mar. 25, 2010, provisional application No. 61/380,981, filed on Sep. 8, 2010, provisional application No. 61/409,106, filed on Nov. 1, 2010, provisional application No. 61/409,473, filed on Nov. 2, 2010, provisional application No. 61/410,769, filed on Nov. 5, 2010, provisional application No. 61/417,241, filed on Nov. 25, 2010.

(51) Int. Cl.
*C12Q 1/68* (2006.01)
*G01N 21/64* (2006.01)

(52) U.S. Cl.
CPC ......... *G01N 21/6486* (2013.01); *C12Q 1/6848* (2013.01); *G01N 21/6428* (2013.01); *G01N 21/6456* (2013.01); *G01N 2021/6441* (2013.01); *G01N 2201/1242* (2013.01)

(58) Field of Classification Search
CPC .......... C12Q 1/6848; C12Q 2545/101; C12Q 2563/107; C12Q 2563/159
USPC ........................................................ 435/6.1
See application file for complete search history.

(56) References Cited

U.S. PATENT DOCUMENTS

| | | |
|---|---|---|
| 3,575,220 A | 4/1971 | Davis et al. |
| 4,051,025 A | 9/1977 | Ito |
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |

(Continued)

FOREIGN PATENT DOCUMENTS

| | | |
|---|---|---|
| EP | 1 522 582 A2 | 4/2005 |
| EP | 1 522 582 B1 | 4/2007 |
| GB | 1 503 163 | 3/1978 |
| GB | 2 097 692 | 11/1982 |
| JP | 0295433 | 4/1990 |

(Continued)

OTHER PUBLICATIONS

J. Smid-Korbar et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.

(Continued)

*Primary Examiner* — Cynthia B Wilder

(74) *Attorney, Agent, or Firm* — Kolisch Hartwell, P.C.

(57) ABSTRACT

System, including methods and apparatus, for performing droplet-based assays that are controlled and/or calibrated using signals detected from droplets.

5 Claims, 15 Drawing Sheets

(56) References Cited

U.S. PATENT DOCUMENTS

| | | |
|---|---|---|
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0089561 A1* | 7/2002 | Weitzel et al. .................. 347/19 |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |

(56) References Cited

U.S. PATENT DOCUMENTS

| | | |
|---|---|---|
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |

(56) References Cited

FOREIGN PATENT DOCUMENTS

| WO | 2006/095981 | 9/2006 |
|---|---|---|
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2011/034621 | 3/2011 |
| WO | 2011/079176 | 6/2011 |

OTHER PUBLICATIONS

A. Chittofrati et al., "Perfluoropolyether microemulsions," Progress in Colloid & Polymer Science 79, pp. 218-225, (1989).
Steven A. Snow, "Synthesis and Characterization of Zwitterionic Silicone Sulfobetaine Surfactants," Langmuir, vol. 6, No. 2, American Chemical Society, pp. 385-391, (1990).
Polydimethylsiloxane, 5 pgs., published in FNP 52 (1992).
Russell Higuchi et al., "Kinetic PCR Analysis: Real-time Monitoring of DNA Amplification Reactions," Bio/Technology vol. II, pp. 1026-1030, Sep. 11, 1993.
D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).
Y. Sela et al., "Newly designed polysiloxane-graft-poly (oxyethylene) copolymeric surfactants: preparation, surface activity and emulsification properties," Colloid & Polymer Science 272, pp. 684-691, (1994).
M. Gasperlin et al., "The structure elucidation of semisolid w/o emulsion systems containing silicone surfactant," International Journal of Pharmaceutics 107, pp. 51-56, (1994).
Mieczyslaw A. Piatyszek et al., "Detection of telomerase activity in human cells and tumors by a telomeric repeat amplification protocol (TRAP)," Methods in Cell Science 17, pp. 1-15, (1995).
Anthony P. Shuber et al., "A Simplified Procedure for Developing Multiplex PCRs," Genome Research, published by Cold Spring Harbor Laboratory Press, pp. 488-493, (1995).
A. V. Yazdi et al., "Highly Carbon Dioxide Soluble Surfactants, Dispersants and Chelating Agents," Fluid Phase Equilibria, vol. 117, pp. 297-303, (1996).
Ariel A. Avilion et al., "Human Telomerase RNA and Telomerase Activity in Immortal Cell Lines and Tumor Tissues," Cancer Research 56, pp. 645-650, Feb. 1, 1996.
Shuming Nie et al., "Optical Detection of Single Molecules," Annu. Rev. Biophys. BiomoL Struct. vol. 26, pp. 567-596, (1997).
Edith J. Singley et al., "Phase behavior and emulsion formation of novel fluoroether amphiphiles in carbon dioxide," Fluid Phase Equilibria 128, pp. 199-219, (1997).
Olga Kalinina et al., "Nanoliter scale PCR with TaqMan Detection," Nucleic Acids Research, vol. 25, No. 10 pp. 1999-2004, (1997).
Zhen Guo et al., "Enhanced discrimination of single nucleotide polymorphisms by artificial mismatch hybridization," Nature Biotechnology vol. 15, pp. 331-335, Apr. 1997.
E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.
Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
Bert Vogelstein et al., "Digital PCR," Proc. Natl. Acad. Sci. USA, vol. 96, pp. 9236-9241, Aug. 1999.
Anthony J. O'Lenick, Jr., "Silicone Emulsions and Surfactants," Journal of Surfactants and Detergents, vol. 3, No. 3, Jul. 2000.
N. Garti et al., "Water Solubilization in Nonionic Microemulsions Stabilized by Grafted Siliconic Emulsifiers," Journal of Colloid and Interface Science vol. 233, pp. 286-294, (2001).
Shinji Katsura et al., "Indirect micromanipulation of single molecules in water-in-oil emulsion," Electrophoresis, vol. 22, pp. 289-293, (2001).
Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).
Hidenori Nagai et al., "Development of a Microchamber Array for Picoliter PCR," Analytical Chemistry, vol. 73, No. 5, pp. 1043-1047, Mar. 1, 2001.
Christopher B. Price, "Regular Review Point of Care Testing," BMJ, vol. 322, May 26, 2001.
3M Specialty Materials, "3M Fluorinert Electronic Liquid FC-3283," product information guide, issued Aug. 2001.
Ivonne Schneegaß et al., "Miniaturized flow-through PCR with different template types in a silicon chip thermocycler," Lab on a Chip, vol. 1, pp. 42-49, (2001).
Randla M. Hill, "Silicone surfactants—new developments," Current Opinion in Colloid & Interface Science 7, pp. 255-261, (2002).
Richard M. Cawthon, "Telomere measurement by quantitative PCR," Nucleic Acids Research, vol. 30, No. 10, pp. 1-6, (2002).
Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).
Shelley L. Anna et al., "Formation of dispersions using "flow focusing" in microchannels," Applied Physics Letters, vol. 82, No. 3, Jan. 20, 2003.
Goldschmidt GmbH, "Abil® EM 90 Emulsifier for the formulation of cosmetic W/O creams and lotions," degussa. creating essentials brochure, pp. 1-7, May 2003.
Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).
R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with M1-PCR," PNAS, vol. 100, No. 13, pp. 7449-7453, Jun. 24, 2003.
Devin Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Groff M. Schroeder et al., "Introduction to Flow Cytometry" version 5.1, 182 pgs. (2004).
Stéphane Swillens et al., "Instant evaluation of the absolute initial number of cDNA copies from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.

(56) References Cited

OTHER PUBLICATIONS

Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative real-time PCR with the prospective of developing automated high-throughput applications," Nucleic Acids Research. vol. 32, No. 22, pp. 1-8, (2004).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 3706-3715, (2005).
Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).
Marcel Margulies et al., "Genome sequencing in microfabricated high-density picolitre reactors," Nature, vol. 437, 51 pgs., Sep. 15, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Toshko Zhelev et al., "Heat Integration in Micro-Fluidic Devices," 16$^{th}$ European Symposium on Computer Aided Process Engineering and 9$^{th}$ International Symposium on Process Systems Engineering, pp. 1863-1868 published by Elsevier B.V. (2006).
Piotr Garstecki et al., "Formation of droplets and bubbles in a microfluidic T-junction—scaling and mechanism of break-up," Lab on a Chip, vol. 6, pp. 437-446, (2006).
Darren R. Link et al., "Electric Control of Droplets in Microfluidic Devices," Angewandte Chemie Int. Ed., vol. 45, pp. 2556-2560, (2006).
Peter Fielden et al., "Micro-Droplet Technology for High Throughout Systems and Methods," 1 pg., Mar. 8, 2006.
David Emerson et al., "Microfluidic Modelling Activities at C3M," Centre for Microfluidics & Microsystems Modelling, Daresbury Laboratory, pp. 1-26, May 15, 2006.
Richard Williams et al., "Amplification of complex gene libraries by emulsion PCR," Nature Methods, vol. 3, No. 7, pp. 545-550, Jul. 2006.
John H. Leamon et al., "Overview: methods and applications for droplet compartmentalization of biology," Nature Methods, vol. 3, No. 7, pp. 541-543, Jul. 2006.
Andrew D. Griffiths et al., "Miniaturising the laboratory in emulsion droplets," TRENDS in Biotechnology, vol. 24, No. 9, pp. 395-402, Jul. 14, 2006.
Jian-Bing Fan et al., "Highly parallel genomic assays," Nature Reviews/Genetics, vol. 7, pp. 632-644, Aug. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanfluid, vol. 3, pp. 239-243, (2007), published online Sep. 22, 2006.
Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.
Kristofer J. Thurecht et al., "Kinetics of Enzymatic Ring-Opening Polymerization of $\in$-Caprolactone in Supercritical Carbon Dioxide," Macromolecules, vol. 39, pp. 7967-7972, (2006).
Machiko Hori et al., "Uniform amplification of multiple DNAs by emulsion PCR," Biochemical and Biophysical Research Communications, vol. 352, pp. 323-328, (2007).
Frank Diehl et al., "Digital quantification of mutant DNA in cancer patients," Current Opinion in Oncology, vol. 19, pp. 36-42, (2007).
Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.
Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Dayong Jin et al., "Practical Time-Gated Luminescence Flow Cytometry. II: Experimental Evaluation Using UV LED Excitation," Cytometry Part A • 71A, pp. 797-808, Aug. 24, 2007.
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Nathan Blow, "PCR's next frontier," Nature Methods, vol. 4, No. 10, pp. 869-875, Oct. 2007.
Nicole Pamme, "continuous flow separations in microfluidic devices," Lab on a Chip, vol. 7, pp. 1644-1659, Nov. 2, 2007.
N. Reginald Beer et al., "On-Chip, Real-Time, Single-Coy Polymerase Chain Reaction in Picoliter Droplets," Analytical Chemistry, vol. 79, No. 22, pp. 8471-8475, Nov. 15, 2007.
Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Sigma-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.

(56) References Cited

OTHER PUBLICATIONS

Somil C. Mehta et a., "Mechanism of Stabilization of Silicone Oil-Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Simant Dube et al., "Mathematical Analysis of Copy Number Variation in a DNA Sample Using Digital PCR on a Nanofluidic Device," PLoS One, vol. 3, Issue 8, pp. 1-9, Aug. 6, 2008.
Jian Qin et al., "Studying copy number variations using a nanofluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May, 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Lee W. Young, Authorized Officer, Commissioner for Patents, U.S. Receiving Office, "International Search Report" in connection with related PCT Patent App. Serial No. PCT/US2009/05317, 2 pgs., Nov. 20, 2009.
Lee W. Young, Authorized Officer, Commissioner for Patents, U.S. Receiving Office, "Written Opinion of the International Searching Authority" in connection with related PCT Patent App. Serial No. PCT/US2009/05317, 7 pgs., Nov. 20, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semisolid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Thinxxs Microtechnology AG, "Emerald Biosystems: Protein Crystallization," 1 pg., downloaded Mar. 8, 2011.
Qun Zhong et al., "Multiplex digital PCR: breaking the one target per color barrier of quantitative PCR," Lab on a Chip, vol. 11, pp. 2167-2174, (2011).
Jiaqi Huang et al., "Rapid Screening of Complex DNA Samples by Single-Molecule Amplification and Sequencing," PLoS ONE, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite™ Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 8-19, Aug. 2012.
A. Scherer, California Institute of Technology, "Polymerase Chain Reactors" PowerPoint presentation, 24 pgs., date unknown.
Eschenback Optik GmbH, Optics for Concentrated Photovoltaics (CPV), 1 pg., date unknown.

\* cited by examiner

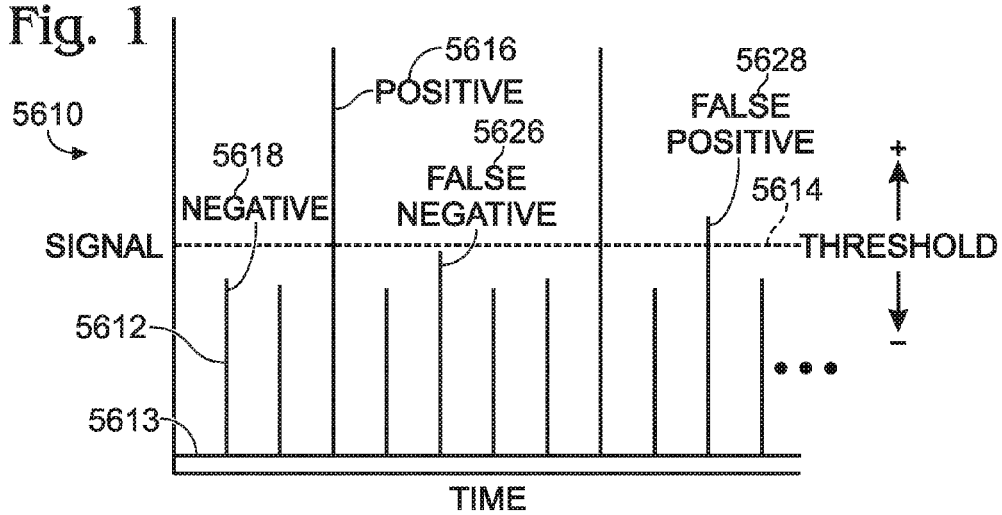
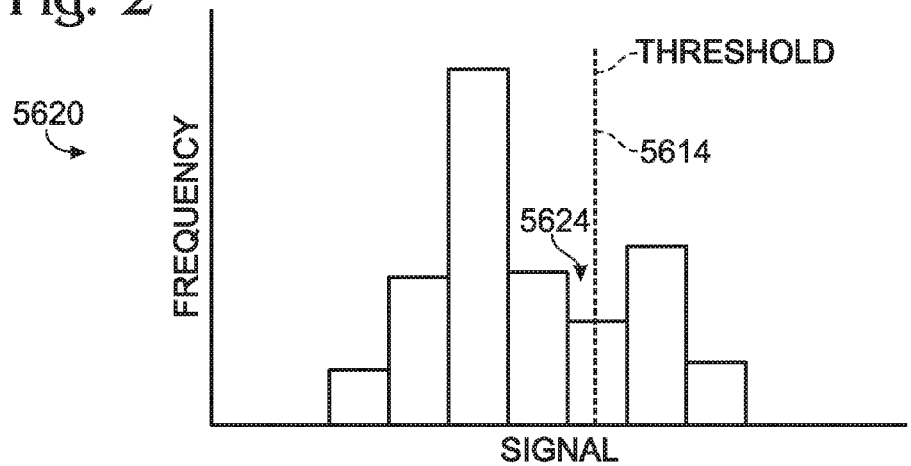

- 5642 PREPARE SAMPLE
- 5644 GENERATE DROPLETS
- 5646 PERFORM REACTION
- 5648 DETECT SIGNAL
- 5650 DETERMINE ASPECT OF ANALYTE

- 5662 FIND DROPLET SIGNALS
- 5664 IDENTIFY POSITIVE DROPLETS
- 5666 COUNT POSITIVE DROPLETS
- 5668 DETERMINE TOTAL NUMBER OF DROPLETS
- 5670 CALCULATE POSITIVE FRACTION
- 5672 OBTAIN CONCENTRATION

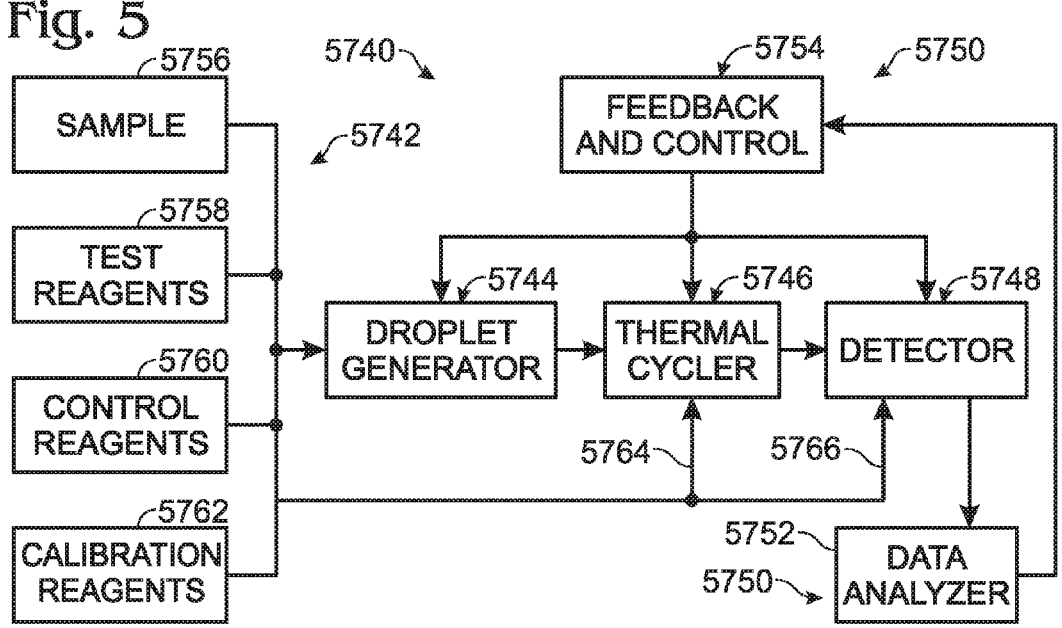

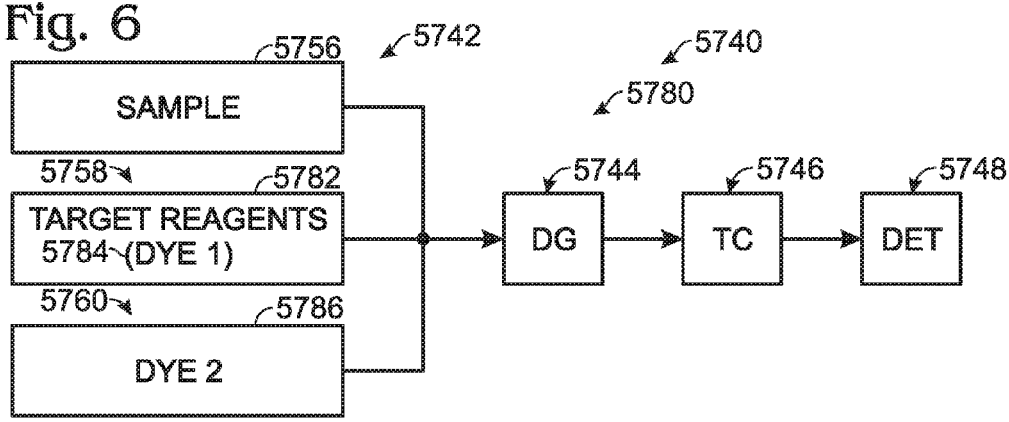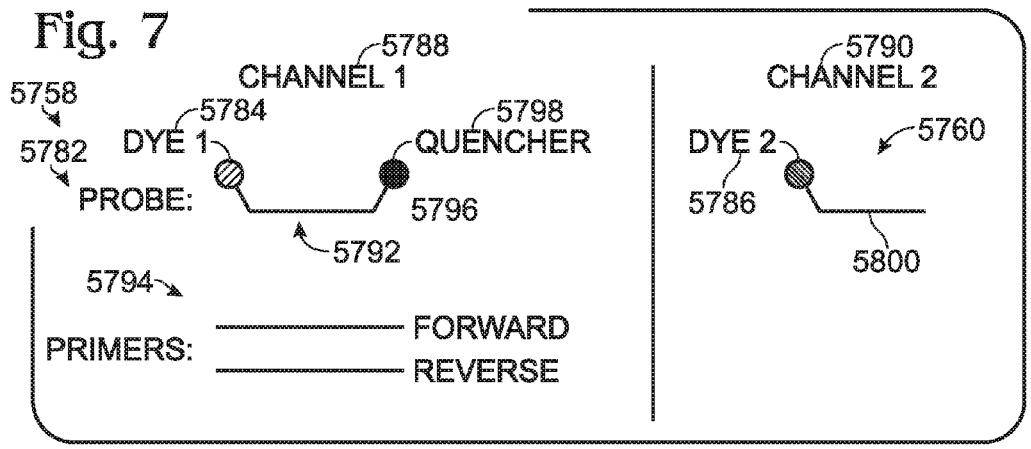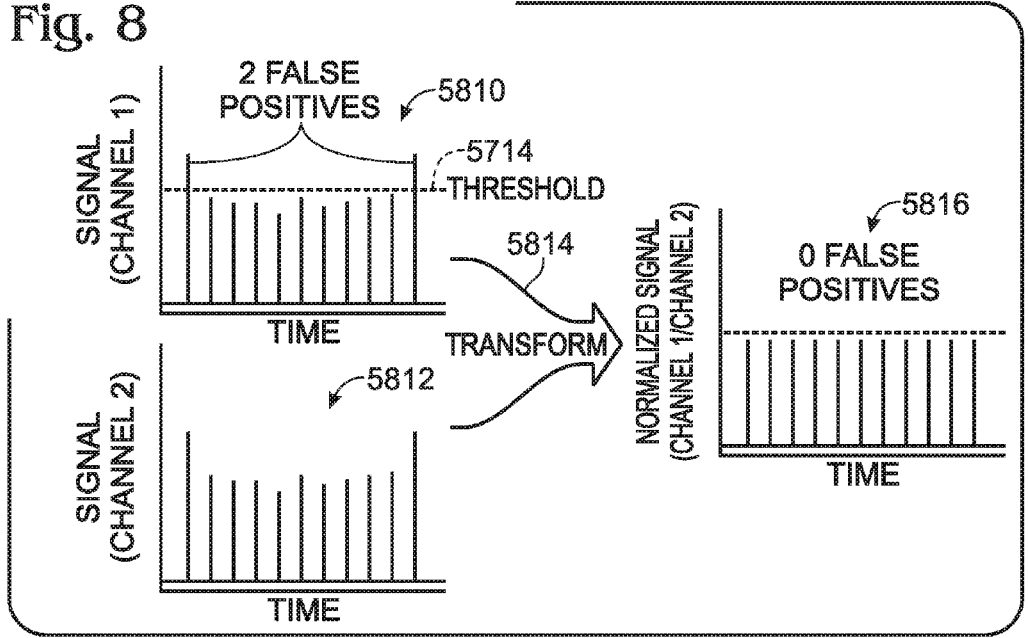

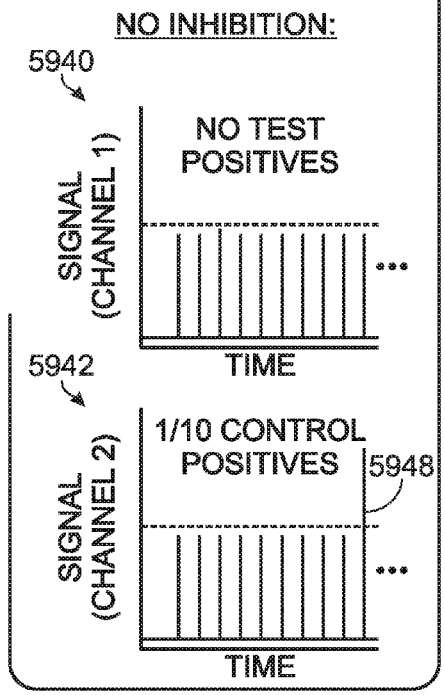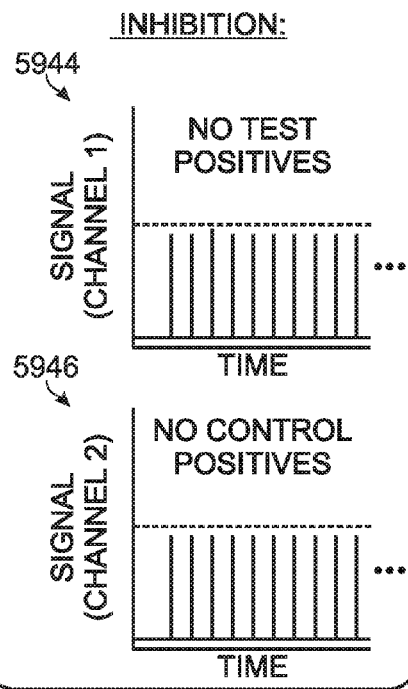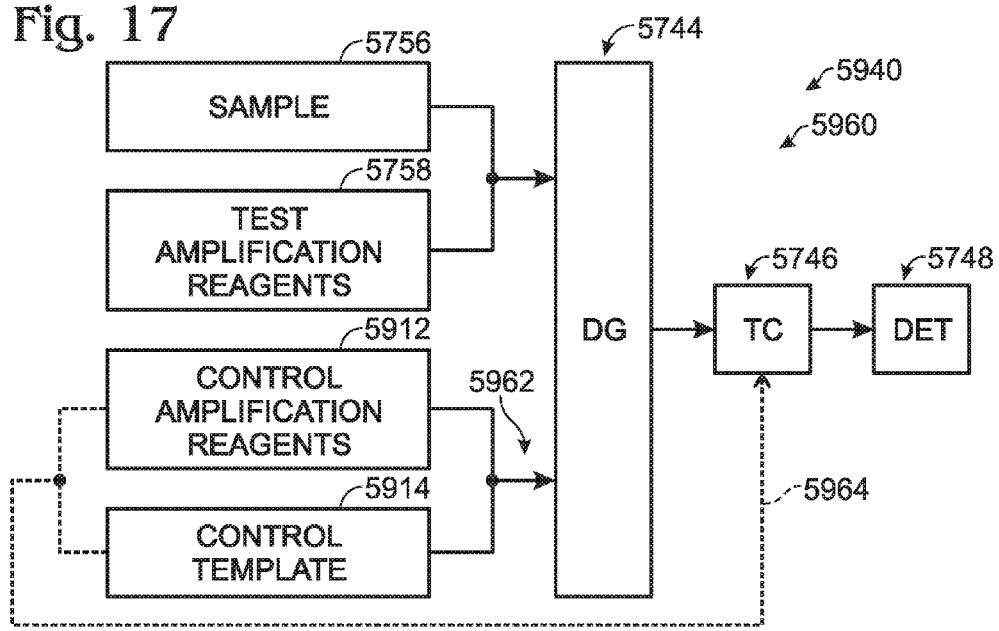

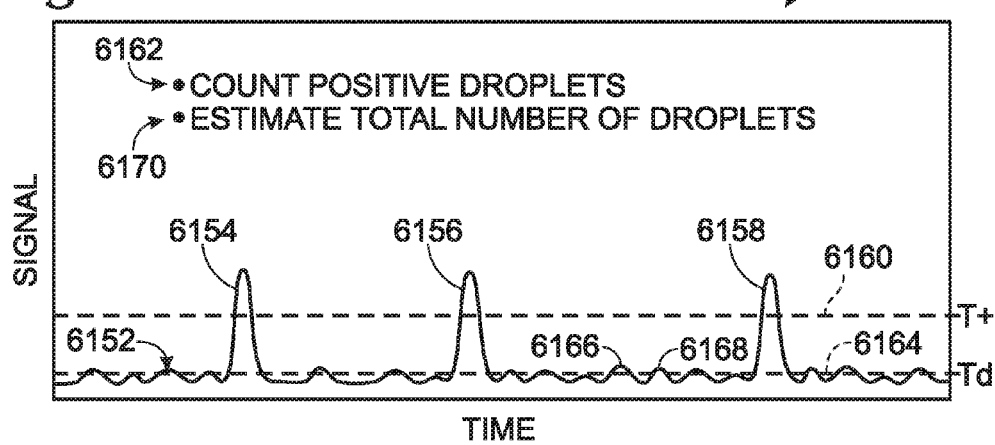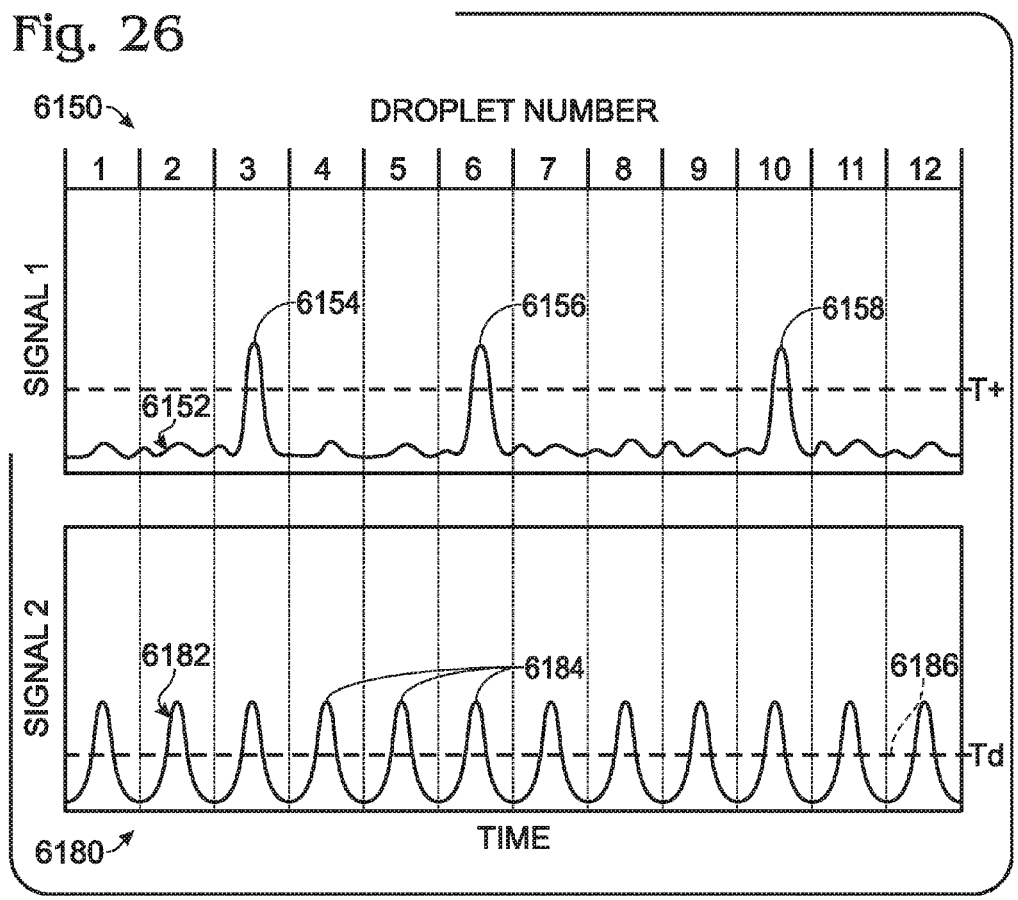

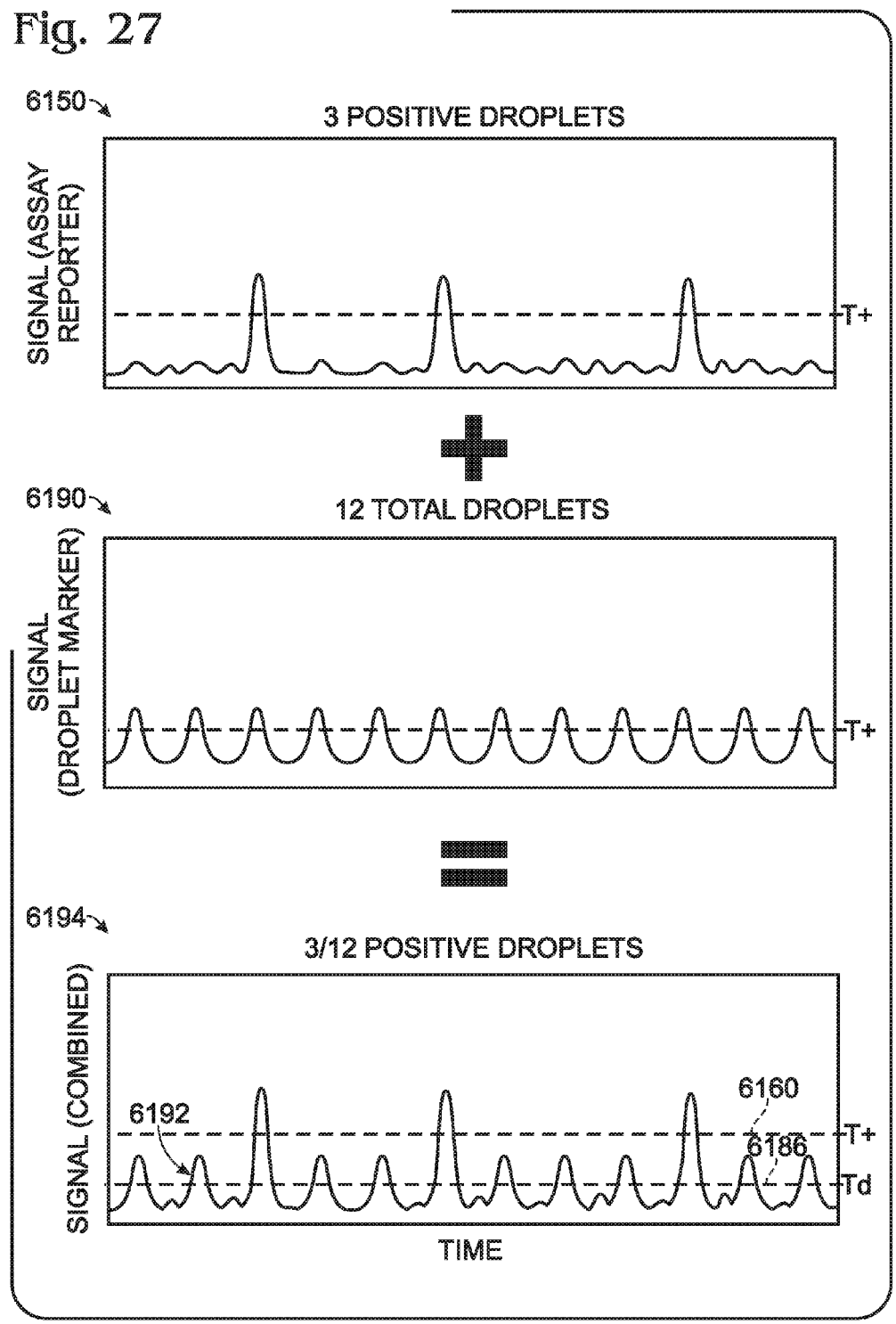

CALIBRATIONS AND CONTROLS FOR DROPLET-BASED ASSAYS

CROSS-REFERENCES TO PRIORITY APPLICATIONS

This application is a continuation-in-part of the following U.S. patent applications: Ser. No. 13/251,016, filed Sep. 30, 2011; Ser. No. 13/245,575, filed Sep. 26, 2011; and Ser. No. 12/976,827, filed Dec. 22, 2010.

U.S. patent application Ser. No. 13/245,575, in turn, is a continuation of U.S. patent application Ser. No. 12/586,626, filed Sep. 23, 2009, which, in turn, is based upon and claims the benefit under 35 U.S.C. §119(e) of the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; and Ser. No. 61/277,270, filed Sep. 22, 2009.

U.S. patent application Ser. No. 12/976,827, in turn, is based upon and claims the benefit under 35 U.S.C. §119(e) of the following U.S. provisional patent applications: Ser. No. 61/309,845, filed Mar. 2, 2010; Ser. No. 61/341,218, filed Mar. 25, 2010; Ser. No. 61/317,635, filed Mar. 25, 2010; Ser. No. 61/380,981, filed Sep. 8, 2010; Ser. No. 61/409,106, filed Nov. 1, 2010; Ser. No. 61/409,473, filed Nov. 2, 2010; Ser. No. 61/410,769, filed Nov. 5, 2010; and Ser. No. 61/417,241, filed Nov. 25, 2010.

These priority applications are incorporated herein by reference in their entireties for all purposes.

CROSS-REFERENCES TO RELATED MATERIALS

This application incorporates by reference in their entireties for all purposes the following materials: U.S. Pat. No. 7,041,481, issued May 9, 2006; U.S. patent application Ser. No. 12/862,542, filed Aug. 24, 2010; and Joseph R. Lakowicz, PRINCIPLES OF FLUORESCENCE SPECTROSCOPY ($2^{nd}$ Ed. 1999).

INTRODUCTION

Droplet-based tests for amplification generally need to be accurate. If inaccurate, these tests can generate erroneous results, that is, false negatives and false positives. Each type of erroneous result can have detrimental consequences. False negatives related to detection of a disease could mean that the disease is not treated early and is permitted to spread. In contrast, false positives could cause unnecessary alarm, potentially triggering an unnecessary response that may be costly and disruptive. To avoid problems associated with false negatives and false positives, inaccurate amplification tests must be repeated to improve their reliability, which increases cost and uses more sample and reagent, each of which may be precious.

FIG. 1 shows a graph 5610 illustrating an exemplary approach for using fluorescence to measure amplification of a nucleic acid target in droplets formed by partitioning a sample. The graph plots, with respect to time, fluorescence signals that may be detected from a flow stream containing the droplets. Each droplet may be detected as a transient change (e.g., a transient increase) in intensity of the fluorescence signal, such as a peak or spike 5612 (i.e., a wave) formed by the fluorescence signal.

To improve clarity, the illustrative data shown here and in other figures of the present disclosure, are presented in a simplified form: each peak has no width and projects from a constant background signal 5613 formed by detection of a continuous phase carrying the droplets. However, a signal peak may have any suitable shape based on, for example, the frequency of detecting signals (the sampling rate), the shape of each droplet, the size and geometry of a channel carrying the flow stream, the flow rate, and the like. Moreover, the signal peaks may have any suitable temporal distribution, for example, occurring at relatively constant intervals, as shown here, or at varying intervals. A droplet signal provided by and/or calculated from the peak (e.g., a signal corresponding to peak height or peak area, among others) may be used to determine whether amplification occurred in the corresponding droplet, and thus whether the droplet received at least one molecule of the nucleic acid target when the sample was partitioned.

Each droplet signal may be compared to a signal threshold 5614, also termed a cutoff. This comparison may provide a determination of whether each droplet signal represents a positive signal (target is present) or a negative signal (target is absent and/or not detected), for amplification in the droplet. For example, droplet signals greater than (and, optionally, equal to) the threshold may be considered as representing positive droplets. Conversely, droplet signals less than (and, optionally, equal to) the threshold may be considered as representing negative droplets. (A positive droplet signal above threshold 5614 is indicated at 5616, and a negative droplet signal below threshold 5614 is indicated at 5618 in FIG. 1.) Comparison to the threshold thus may transform each droplet signal to a digital value, such as a binary value (e.g., a "1" for a positive droplet and "0" for a negative droplet). In any event, the fraction of droplets that are positive can be determined. For a given droplet size, the fraction of positive droplets can be used as an input to an algorithm based on Poisson statistics to determine the number of copies (molecules) of the nucleic acid target present in the initial sample volume. In some embodiments, more than one threshold may be used to categorize results (e.g., negative, positive, or inconclusive).

FIG. 2 shows an exemplary histogram 5620 of ranges of droplet signal intensities that may be measured from the flow stream of FIG. 1. The relative frequency of occurrence of each range is indicated by bar height. The distribution of positive and negative signal intensities may be larger than the modest difference in signal intensity produced by amplification (a positive droplet) relative to no amplification (a negative droplet). Thus, the distributions of droplet signals from positive droplets and negative droplets may produce a problematic overlap between the amplification-positive and amplification-negative droplet signals, indicated at 5624. Accordingly, as shown in FIG. 1, some amplification-positive droplets may provide relatively weak droplet signals, such as false-negative signal 5626, that are less than threshold 5614, resulting in incorrect identification of these positive droplets as negative. Conversely, some amplification-negative droplets may provide relatively strong droplet signals, such as false-positive signal 5628, that are greater than threshold 5614, resulting in incorrect identification of these negative droplets as positive. Since either type of erroneous result may be costly and harmful, it is desirable to minimize their occurrence.

There are many factors that can lead to variation in the fluorescence signal from droplets tested for amplification. Examples of physical parameters that may affect the fluorescence signal may include droplet position when detected (e.g., relative to the "sensed volume" of the detector), droplet volume and shape, optical alignment of detection optics (including excitation source, filters, and detector), detector response, temperature, vibration, and flow rate, among others. Examples of reaction chemistry parameters that may affect the fluorescence signal include the number of target molecules and/or the amount of background nucleic acid present in each droplet, amplification efficiency, batch-to-batch variations in reagent concentrations, and volumetric variability in reagent and sample mixing, among others. Variations in these physical and chemical parameters can increase the overlap in the distribution of positive and negative droplet signals, which can complicate data interpretation and affect test performance (e.g., affect the limit of detection). The variations can occur within a run and/or between runs, within a test on a target and/or between tests on different targets, on the same instrument and/or different instruments, with the same operator and/or different operators, and so on.

Thus, there is a need for improved accuracy and reliability in droplet-based amplification tests. For example, it would be desirable to have droplet-based controls for these tests, optionally, droplet-based controls that can be incorporated into test droplets or incorporated into control droplets that can be intermixed with test droplets. Such integrated controls may have the benefit of reducing cost by processing control reactions in parallel with test reactions, which may speed the analysis. It also would be useful to have one or more controls that can be used to verify hardware, reagent, and/or software (e.g., algorithm) performance.

SUMMARY

The present disclosure provides a system, including methods and apparatus, for performing droplet-based assays that are controlled and/or calibrated using signals detected from droplets.

BRIEF DESCRIPTION OF THE DRAWINGS

FIG. 1 is an exemplary graph of fluorescence signals that may be measured with respect to time from a flow stream of droplets, with the graph exhibiting a series of peaks representing droplet signals, and with the graph indicating a signal threshold for assigning droplet signals as corresponding to amplification-positive and amplification-negative droplets, in accordance with aspects of the present disclosure.

FIG. 2 is an exemplary histogram of ranges of droplet signal intensities that may be measured from the flow stream of FIG. 1, with the relative frequency of occurrence of each range indicated by bar height, in accordance with aspects of the present disclosure.

FIG. 3 is a flowchart illustrating an exemplary method of performing a droplet-based assay, in accordance with aspects of the present disclosure.

FIG. 4 is a flowchart illustrating an exemplary method of determining a concentration of a target, which may be performed as a step in the method of FIG. 3, in accordance with aspects of the present disclosure.

FIG. 5 is a schematic view of an exemplary system for performing droplet-based tests of nucleic acid amplification with the aid of controls and/or calibrators, in accordance with aspects of the present disclosure.

FIG. 6 is a schematic view of selected aspects of the system of FIG. 5, with the system in an exemplary configuration for detecting amplification of a nucleic acid target using a first dye, and for controlling for system variation during a test using a second dye, in accordance with aspects of present disclosure.

FIG. 7 is a schematic view of exemplary reagents that may be included in the system configuration of FIG. 6, to permit detection of amplification signals in a first detection channel and detection of a passive control signals in a second detection channel, in accordance with aspects of present disclosure.

FIG. 8 a flowchart of an exemplary approach to correcting for system variation using the system configuration of FIG. 6, in accordance with aspects of the present disclosure.

FIG. 15 is a pair of exemplary graphs of fluorescence signals that may be detected over time from a flow stream of the system configuration of FIG. 12 or 13 using different detection channels, with one of the channels detecting successful amplification of a control target, thereby indicating no inhibition of amplification, in accordance with aspects of present disclosure.

FIG. 16 is a pair of exemplary graphs with fluorescence signals detected generally as in FIG. 15, but with control signals indicating that amplification is inhibited, in accordance with aspects of present disclosure.

FIG. 17 is a schematic view of selected aspects of the system of FIG. 5, with the system in an exemplary configuration for testing amplification of a pair of nucleic acid targets using a different set of droplets for each target, in accordance with aspects of present disclosure.

FIG. 25 is a graph of an exemplary signal that may be measured with respect to time from a fluid stream containing droplets, with positive droplets forming signal peaks that are identified reliably and negative droplets forming signal peaks that cannot be identified reliably, in accordance with aspects of the present disclosure.

FIG. 26 is a pair of graphs of exemplary first and second signals that may be measured with respect to time from a fluid stream containing droplets, with positive droplets identified using the first signal and the total number of droplets identified using the second signal, in accordance with aspects of the present disclosure.

FIG. 27 is a series of graphs illustrating an exemplary assay-reporter signal and an exemplary droplet-marker signal, which collectively produce a combined signal that may be measured with respect to time in the same detection channel from a fluid stream containing droplets, in accordance with aspects of the present disclosure.

DETAILED DESCRIPTION

Figure 9:
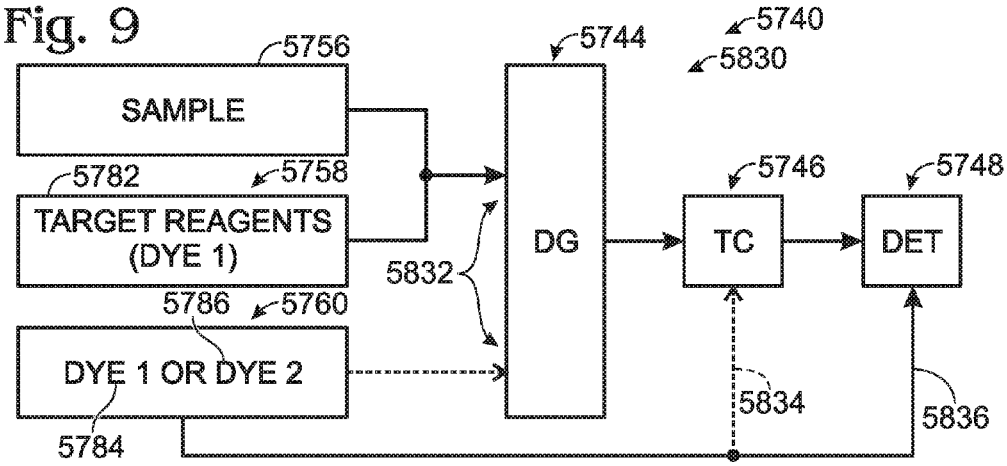
FIG. 9 is a schematic view of selected aspects of the system of FIG. 5, with the system in an exemplary configuration for detecting amplification of a nucleic acid target using a first dye in a set of droplets, and for (a) calibrating the system before, during, and/or after a test or (b) controlling for aspects of system variation during a test using either the first dye or a second dye in another set of droplets, in accordance with aspects of present disclosure.

The present disclosure provides a system, including methods and apparatus, for performing droplet-based assays that are controlled and/or calibrated using signals detected from droplets.

A method of performing a droplet-based assay is provided. In the method, a first signal and a second signal may be detected from a plurality of droplets. Accepted droplets of the plurality may be identified, with the first signal from the accepted droplets meeting a predefined condition. Rejected droplets of the plurality also may be identified, with the first signal from the rejected droplets failing to meet the predefined condition. A concentration of a target in the accepted droplets may be determined based on the second signal from the accepted droplets, and without any contribution of the second signal from the rejected droplets.

Another method of performing a droplet-based assay is provided. In the method, a plurality of droplets containing an assay reporter and a droplet marker may be generated. A signal may be detected from the plurality of droplets, with the signal representing combined emission of light from the assay reporter and the droplet marker. The assay reporter may provide a first integral portion of the signal having an intensity that varies according to whether or not a target is present in a droplet. The droplet marker may provide a second integral portion of the signal having an intensity that is at least substantially independent of whether or not the target is present in a droplet. A number of the plurality of droplets that are positive or a number that are negative for the target based on the signal may be counted. A total number for the plurality of droplets may be determined based on the signal. A concentration of the target may be obtained based on the counted number of droplets and the total number of droplets.

Yet another method of performing a droplet-based assay is provided. In the method, a signal may be detected from a plurality of droplets. Droplets positive for a target may be determined based on the signal. The positive droplets may be counted to establish a number of positive droplets. A total number for the plurality of droplets may be estimated. A concentration of the target may be obtained based on the number of positive droplets and the total number of droplets.

Still another method of performing a droplet-based assay is provided. In the method, a first signal may be detected from a plurality of droplets. Droplets positive for a target may be determined based on the first signal. The positive droplets may be counted to establish a number of positive droplets. A second signal may be detected from the plurality of droplets. The second signal may have an intensity corresponding to a size of each droplet and substantially independent of whether or not the target is present in such droplet. A total number for the plurality of droplets may be determined based on the second signal. A concentration of the target in the plurality of droplets may be obtained based on the number of positive droplets and the total number of droplets.

The present disclosure provides a method of sample analysis.

Droplets may be obtained. The droplets may be generated on-line or at least a subset of the droplets may be pre-formed off-line. At least a subset or all of the droplets may include a partition of a sample to be tested and may be capable of amplification of at least one test nucleic acid target, if present, in the partition. In some embodiments, the droplets may be capable of amplification of a test nucleic acid target and a control nucleic acid target. The droplets collectively or each may include a dye, or at least a first dye and a second dye. In some embodiments, the droplets may be of at least two types, such as two or more types of test droplets, test droplets and calibration droplets, or test droplets and control droplets, among others. In some embodiments, the two or more types of droplets may be distinguishable based on distinct temporal positions of the droplets types in a flow stream, the presence of respective distinct dyes in the droplet types, distinguishable signal intensities of the same dye (or different dyes), or a combination thereof, among others.

Signals, such as fluorescence signals, may be detected from the droplets. The signals may include test signals, calibration signals, control signals, reference signals, or any combination thereof. In some embodiments, test signals and control signals may indicate respectively whether amplification of a test nucleic acid target and a control nucleic acid target occurred in individual droplets. In some embodiments, detection may include (a) exciting first and second dyes with a same wavelength of excitation light and (b) detecting emitted light from the first and second dyes at least substantially independently from one another in respective first and second detection channels.

The signals detected may be analyzed to determine a test result related to a presence (number, concentration, etc.), if any, of a test nucleic acid target in the sample. In some embodiments, analysis may include transforming test signals based on reference signals to reduce variation in the test signals. The test signals and the reference signals may be detected in respective distinct detection channels or in the same detection channel. In some embodiments, the reference signals may be provided by a second dye that is not coupled to an amplification reaction and thus serves as a passive reference. In some embodiments, the reference signals may be provided by control signals detected from a control amplification reaction. The control amplification reaction may measure amplification of an exogenous or endogenous template. In some embodiments, analysis may include (a) comparing test signals, or a transformed set of the test signals, to a signal threshold to assign individual droplets as positive or negative for a test nucleic acid target, and (b) estimating a number of molecules of the test nucleic acid target in the sample based on the comparison. In some embodiments, analysis may include (a) analyzing control signals to determine a control value corresponding to a number and/or fraction of the droplets that are amplification-positive for a control nucleic acid target, and (b) interpreting a test result, such as determining its validity, based on the control value.

The systems disclosed herein may offer improved instrument calibration and/or substantial improvements in the accuracy and/or reliability of droplet-based amplification tests. Exemplary capabilities offered by the present disclosure may include any combination of (1) correcting/minimizing variations in the fluorescence signal to increase the accuracy of droplet PCR results; (2) providing an internal indicator of whether nucleic acid amplification failed (e.g., PCR inhibition from interfering components in the sample, incorrect sample and reagent mixing, incorrect thermal cycling, incorrect droplet formation); (3) providing measurement of droplet volumes without having to add additional hardware components; (4) providing measurement of changes in the baseline fluorescence signal (i.e., baseline drift); (5) providing calibration of a droplet detector before and/or during a run; (6) monitoring the performance of quantitative droplet PCR measurements and data processing algorithms before and/or during a run; (7) verification of droplet integrity (e.g., absence of coalescence); (8) obtaining information on droplet generation and detection frequency (spatially and temporally) using an in-line detector; (9) measuring variations and comparing them to predefined tolerances; (10) processing of raw droplet PCR data to correct for variations and increase test accuracy and performance; (11) incorporating control assays preferably using a single excitation source; and/or (12) quantifying one or more genetic targets by amplifying more than one genetic target in a single droplet.

Further aspects of the present disclosure are presented in the following sections: (I) definitions, (II) system overview, (III) exemplary instrument controls and calibrators, (IV) exemplary amplification controls, (V), exemplary multichannel detection, (VI) exemplary self-normalization of test signals, (VII) examples, and (VIII) detection systems.

I. Definitions

Technical terms used in this disclosure have the meanings that are commonly recognized by those skilled in the art. However, the following terms may have additional meanings, as described below.

Emulsion—a composition comprising liquid droplets disposed in an immiscible liquid. The droplets are formed by at least one dispersed phase, and the immiscible liquid forms a continuous phase. The continuous phase can also or alternatively be termed a carrier and/or a carrier phase. The dispersed phase (or at least one of the dispersed phases of a multiple emulsion) is immiscible with the continuous phase, which means that the dispersed phase (i.e., the droplets) and the continuous phase (i.e., the immiscible liquid) do not mix to attain homogeneity. The droplets are isolated from one another by the continuous phase and enclosed/surrounded by the continuous phase.

The droplets of an emulsion may have any uniform or non-uniform distribution in the continuous phase. If non-uniform, the concentration of the droplets may vary to provide one or more regions of higher droplet density and one or more regions of lower droplet density in the continuous phase. For example, droplets may sink or float in the continuous phase.

An emulsion may be monodisperse, that is, composed of droplets of uniform size, or may be polydisperse, that is, composed of droplets of various sizes. If monodisperse, the droplets of the emulsion may vary in size by a standard deviation of the volume (or diameter) that is less than about 50%, 20%, 10%, 5%, 2%, or 1% of the average droplet volume (or diameter). Droplets generated from an orifice may be monodisperse or polydisperse.

An emulsion may have any suitable composition. The emulsion may be characterized by the predominant liquid compound or type of liquid compound in each phase. The predominant liquid compounds in the emulsion may be one or more aqueous phases and one or more nonaqueous phases. The nonaqueous phase may be referred to as an oil phase comprising at least one oil, which generally includes any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others.

In exemplary embodiments, the oil is a fluorinated oil, such as a fluorocarbon oil, which may be a perfluorinated organic solvent. A fluorinated oil may be a base (primary) oil or an additive to a base oil, among others. Exemplary fluorinated oils that may be suitable are sold under the trade name FLUORINERT (3M), including, in particular, FLUORINERT Electronic Liquid FC-3283, FC-40, FC-43, and FC-70. Another example of an appropriate fluorinated oil is sold under the trade name NOVEC (3M), including NOVEC HFE 7500 Engineered Fluid.

Droplet—a small volume of a first liquid that is enclosed by an immiscible second liquid, such as a continuous phase of an emulsion (and/or by a larger droplet). The volume of a droplet, and/or the average volume of droplets in an emulsion, may, for example, be less than about one microliter (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) may have a diameter (or an average diameter) of less than about 1000, 100, or 10 micrometers, about 1000 to 10 micrometers, or about 500 to 1 micrometers, among others. A droplet may be spherical or nonspherical. A droplet may be a simple droplet or a compound droplet.

Surfactant—a surface-active substance capable of reducing the surface tension of a liquid in which it is present. A surfactant, which also or alternatively may be described as a detergent and/or a wetting agent, may incorporate both a hydrophilic portion and a hydrophobic portion, which may collectively confer a dual hydrophilic-hydrophobic character on the surfactant. A surfactant may, in some cases, be characterized according to its hydrophilicity relative to its hydrophobicity. Each dispersed and/or continuous phase may incorporate at least one surfactant. Each aqueous phase may include at least one nonionic surfactant and/or ionic surfactant. In some embodiments, the aqueous phase may include a surfactant that is a block copolymer of polypropylene oxide and polyethylene oxide. More particularly, the surfactant may be a block copolymer of polypropylene oxide and polyethylene oxide sold under the trade names PLURONIC and TETRONIC (BASF). In some embodiments, the surfactant may be a nonionic block copolymer of polypropylene oxide and polyethylene oxide sold under the trade name PLURONIC F-68. In some embodiments, the surfactant of the aqueous phase may be a water-soluble and/or hydrophilic fluorosurfactant. Exemplary fluorosurfactants for the aqueous phase are sold under the trade name ZONYL (DuPont), such as ZONYL FSN fluorosurfactants. In some cases, the surfactant may include polysorbate 20 (sold under the trade name TWEEN-20 by ICI Americas, Inc.). An exemplary concentration of surfactant for the aqueous phase is about 0.01 to 10%, 0.05 to 5%, 0.1 to 1%, or 0.5% by weight, among others.

A nonaqueous or oil phase may incorporate a hydrophobic surfactant. The nonaqueous phase may include one or more surfactants. The surfactants may include a nonionic surfactant, an ionic surfactant (a cationic (positively-charged) or anionic (negatively-charged) surfactant), or both types of surfactant. Exemplary anionic surfactants that may be suitable include carboxylates, sulphonates, phosphonates, and so on. The one or more surfactants may be present, individually or collectively, at any suitable concentration, such as greater than about 0.001% or 0.01%, or about 0.001% to 10%, 0.05% to 2%, or 0.05% to 0.5%, among others.

The one or more surfactants present in the nonaqueous phase (or oil phase) may be fluorinated surfactants (e.g., surfactant compounds that are polyfluorinated and/or perfluorinated). Exemplary fluorinated surfactants are fluorinated polyethers, such as carboxylic acid-terminated perfluoropolyethers, carboxylate salts of peril uoropolyethers, and/or amide or ester derivatives of carboxylic acid-terminated perfluoropolyethers. Exemplary but not exclusive perfluoropolyethers are commercially available under the trade name KRYTOX (DuPont), such as KRYTOX-FSH, the ammonium salt of KRYTOX-FSH ("KRYTOX-AS"), or a morpholino derivative of KRYTOX-FSH ("KRYTOX-M"), among others. Other fluorinated polyethers that may be suitable include at least one polyethylene glycol (PEG) moiety.

Fluorinated—including fluorine, typically substituted for hydrogen. Any of the fluorinated compounds disclosed herein may be polyfluorinated, meaning that such compounds each include many fluorines, such as more than five or ten fluorines, among others. Any of the fluorinated compounds disclosed herein also or alternatively may be perfluorinated, meaning that most or all hydrogens have been replaced with fluorine.

Analyte—a component(s) or potential component(s) of a sample that is analyzed in a test. An analyte is a specific subject of interest in a test where the sample is the general subject of interest. An analyte may, for example, be a nucleic acid, protein, peptide, enzyme, cell, bacteria, spore, virus, organelle, macromolecular assembly, drug candidate, lipid, carbohydrate, metabolite, or any combination thereof, among others. The analyte itself may be described as a target, or a target may represent the analyte. An analyte (and/or target) may be tested for any suitable aspect, such as its presence, activity, interaction with (e.g., binding to) one or more other components, and/or other characteristic in a sample and/or in partitions thereof. The presence of an analyte (and/or target) may relate to an absolute or relative number, concentration, binary assessment (e.g., present or absent), or the like, of the analyte (or target) in a sample or in one or more partitions thereof. In some examples, a sample may be partitioned (e.g., to create droplets) such that a copy of the analyte (or target) is not present in all of the partitions, such as being present in the partitions at an average concentration of about 0.0001 to 10,000, 0.001 to 1000, 0.01 to 100, or 0.1 to 10 copies (or molecules) per partition, or at an average concentration of less than about 10 copies, 2 copies, or 1 copy per partition. In some examples, a sample may be partitioned such that at least one or a plurality of the partitions include no copies (or molecules) of the analyte (or target) and/or such that at least one or a plurality of the partitions include only one copy (or molecule) of the analyte (or target).

Reaction—a chemical reaction, a binding interaction, a phenotypic change, or a combination thereof, which generally provides a detectable signal (e.g., a fluorescence signal) indicating occurrence and/or an extent of occurrence of the reaction. An exemplary reaction is an enzyme reaction that involves an enzyme-catalyzed conversion of a substrate to a product.

Any suitable enzyme reactions may be performed in the droplet-based assays disclosed herein. For example, the reactions may be catalyzed by a kinase, nuclease, nucleotide cyclase, nucleotide ligase, nucleotide phosphodiesterase, polymerase (DNA or RNA), prenyl transferase, pyrophosphatase, reporter enzyme (e.g., alkaline phosphatase, beta-galactosidase, chloramphenicol acetyl transferse, glucuronidase, horse radish peroxidase, luciferase, etc.), reverse transcriptase, topoisomerase, etc.

Sample—a compound, composition, and/or mixture of interest, from any suitable source(s). A sample is the general subject of interest for a test that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, pre-amplification (e.g., to achieve target enrichment by performing limited cycles (e.g., <15) of PCR on sample prior to PCR), removal of amplicon (e.g., treatment with uracil-d-glycosylase (UDG) prior to PCR to eliminate any carry-over contamination by a previously generated amplicon (i.e., the amplicon is digestable with UDG because it is generated with dUTP instead of dTTP)), partitioning, or any combination thereof, among others. Clinical samples may include and/or may be provided by a nasopharyngeal wash, blood, plasma, cell-free plasma, buffy coat, saliva, urine, stool, sputum, mucous, a wound swab, a tissue biopsy, milk, a fluid aspirate, a swab (e.g., a nasopharyngeal swab), and/or tissue, among others. Environmental samples may include water, soil, aerosol, and/or air, among others. Research samples may include cultured cells, primary cells, bacteria, spores, viruses, small organisms, any of the clinical samples listed above, or the like. Additional samples may include foodstuffs, weapons components, biodefense samples to be tested for bio-threat agents, suspected contaminants, and so on.

Samples may be collected for diagnostic purposes (e.g., the quantitative measurement of a clinical analyte such as an infectious agent) or for monitoring purposes (e.g., to determine that an environmental analyte of interest such as a bio-threat agent has exceeded a predetermined threshold).

Reagent—a compound, set of compounds, and/or composition that is combined with a sample in order to perform a particular test(s) on the sample. A reagent may be a target-specific reagent, which is any reagent composition that confers specificity for detection of a particular target(s) or analyte(s) in a test. A reagent optionally may include a chemical reactant and/or a binding partner for the test. A reagent may, for example, include at least one nucleic acid, protein (e.g., an enzyme), cell, virus, organelle, macromolecular assembly, drug candidate, lipid, carbohydrate, inorganic substance, or any combination thereof, and may be an aqueous composition, among others. In exemplary embodiments, the reagent may be an amplification reagent, which may include at least one primer or at least one pair of primers for amplification of a nucleic acid target, at least one probe and/or dye to enable detection of amplification, a polymerase, a ligase, nucleotides (dNTPs and/or NTPs), divalent magnesium ions, or any combination thereof, among others. In some embodiments, the reagent may be a PCR reagent, namely, a reagent involved in PCR amplification, such as a primer, a heat-stable polymerase, at least one nucleotide (dNTP or NTP), or magnesium, among others. An amplification reagent and/or a nucleic acid target each may be described as a reaction component.

The amplification reagent may be present at an effective amount, namely, an amount sufficient to enable amplification of a nucleic acid target in the presence of other necessary reagents. Exemplary effective amounts of PCR reagents are as follows: heat-stable DNA polymerase, 0.005 to 0.5 Units/µL; dNTPs, 50 µM to 5 mM each; primers, 0.02 to 5.0 µM each; and $Mg^{2+}$, 0.5 to 10 mM.

Nucleic acid—a compound comprising a chain of nucleotide monomers. A nucleic acid may be single-stranded or double-stranded, among others. The chain of a nucleic acid may be composed of any suitable number of monomers, such as at least about ten or one-hundred, among others. Generally, the length of a nucleic acid chain corresponds to its source, with synthetic nucleic acids (e.g., primers and probes) typically being shorter, and biologically/enzymatically generated nucleic acids (e.g., nucleic acid analytes) typically being longer.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acids (LNA), threose nucleic acids (TNA), and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of such base pairs with the other nucleic acid is termed "complementary."

Replication—a process forming a copy (i.e., a direct copy and/or a complementary copy) of a nucleic acid or a segment thereof. Replication generally involves an enzyme, such as a polymerase and/or a ligase, among others. The nucleic acid and/or segment replicated is a template (and/or a target) for replication.

Amplification—a reaction in which replication occurs repeatedly over time to form multiple copies of at least one segment of a template molecule. Amplification may generate an exponential or linear increase in the number of copies as amplification proceeds. Typical amplifications produce a greater than 1,000-fold increase in copy number. Exemplary amplification reactions for the assays disclosed herein may include the polymerase chain reaction (PCR) or ligase chain reaction (LCR), each of which is driven by thermal cycling. Thermal cycling generally involves cycles of heating and cooling a reaction mixture to perform successive rounds of denaturation (melting), annealing, and extension. The assays also or alternatively may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification may utilize a linear or circular template.

Amplification may be performed with any suitable reagents. Amplification may be performed, or tested for its occurrence, in an amplification mixture, which is any composition capable of generating multiple copies of a nucleic acid target molecule (or region thereof), if present, in the composition. An amplification mixture may include any combination of at least one primer or primer pair, at least one probe, at least one replication enzyme (e.g., at least one polymerase, such as at least one DNA and/or RNA polymerase, and/or at least one ligase), and/or deoxynucleotide (and/or nucleotide) triphosphates (dNTPs and/or NTPs), among others.

PCR—nucleic acid amplification that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a heat-stable polymerase, such as Taq DNA polymerase (e.g., wild-type enzyme, a Stoffel fragment, Fast-Start polymerase, etc.), Pfu DNA polymerase, S-Tbr polymerase, Tth polymerase, Vent polymerase, or a combination thereof, among others. PCR generally produces an exponential increase in the amount of a product amplicon over successive cycles.

Any suitable PCR methodology or combination of methodologies may be utilized in the assays disclosed herein, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, universal fast walking PCR, or any combination thereof, among others.

Amplicon—a product of an amplification reaction. An amplicon may be single-stranded or double-stranded, or a combination thereof. An amplicon corresponds to any suitable segment or the entire length of a nucleic acid target.

Primer—a nucleic acid capable of, and/or used for, priming replication of a nucleic acid template. Thus, a primer may be a shorter nucleic acid that is complementary to a longer template. During replication, the primer may be extended, based on the template sequence, to produce a longer nucleic acid that is a complementary copy of the template. Extension may occur by successive addition of individual nucleotides (e.g., by the action of a polymerase) or by attachment of a block of nucleotides (e.g., by the action of a ligase joining a pair of primers), among others. A primer may be DNA, RNA, an analog thereof (i.e., an artificial nucleic acid), or any combination thereof. A primer may have any suitable length, such as at least about 10, 15, 20, or 30 nucleotides. Exemplary primers are synthesized chemically. Primers may be supplied as at least one pair of primers for amplification of at least one nucleic acid target. A pair of primers may be a sense primer and an antisense primer that collectively define the opposing ends (and thus the length) of a resulting amplicon.

Probe—a nucleic acid connected to at least one label, such as at least one dye. A probe may be a sequence-specific binding partner for a nucleic acid target and/or amplicon. The probe may be designed to enable detection of target amplification based on fluorescence resonance energy transfer (FRET). An exemplary probe for the nucleic acid assays disclosed herein includes one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe). The nucleic acid portion of the probe may have any suitable structure or origin, for example, the portion may be a locked nucleic acid, a member of a universal probe library, or the like. In other cases, a probe and one of the primers of a primer pair may be combined in the same molecule (e.g., AMPLIFLUOR primers or SCORPION primers). As an example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)). Another exemplary probe for droplet-based nucleic acid assays is a Plexor primer. Some reagents that are termed "probes," such as molecular inversion probes, may not include a label (e.g., may include no dye).

Label—an identifying and/or distinguishing marker or identifier connected to or incorporated into any entity, such as a compound, biological particle (e.g., a cell, bacteria, spore, virus, or organelle), or droplet. A label may, for example, be a dye that renders an entity optically detectable and/or optically distinguishable. Exemplary dyes used for labeling are fluorescent dyes (fluorophores) and fluorescence quenchers. The dye may be a compound, only part of a compound (i.e., a moiety), or the like.

The label may be a droplet marker that marks the position of each droplet, e.g., in a flow stream or field of view, among others. A droplet marker may have any suitable uniform or nonuniform distribution in each droplet. For example, the droplet marker may be distributed substantially uniformly throughout a droplet, may be localized to a perimeter of the droplet (e.g., localized to a skin that encapsulates the droplet), or may have one or more discrete localizations within the droplet (e.g., if the marker is a particle (such as a bead or quantum dot, among others)). Further aspects of a skin that encapsulates droplets are disclosed in U.S. patent application Ser. No. 12/976,827, filed Dec. 22, 2010, which is incorporated herein by reference.

Reporter—a compound or set of compounds that reports a condition, such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR Green, ethidium bromide, etc.).

Binding partner—a member of a pair of members that bind to one another. Each member may be a compound or biological particle (e.g., a cell, bacteria, spore, virus, organelle, or the like), among others. Binding partners may bind specifically to one another. Specific binding may be characterized by a dissociation constant of less than about $10^{-4}$, $10^{-6}$, $10^{-8}$, or $10^{-10}$ M, among others. Exemplary specific binding partners include biotin and avidin/streptavidin, a sense nucleic acid and a complementary antisense nucleic acid (e.g., a probe and an amplicon), a primer and its target, an antibody and a corresponding antigen, a receptor and its ligand, and the like.

Signal—detectable and/or detected energy and/or information. Any of the signals detected, after detection, may be described as signals and/or data. For example, detected droplet signals may provide test signals and test data, control signals or control data, reference signals and reference data, calibration signals and calibration data, transformed signals and transformed data, or any combination thereof, among others. A signal may be detected optically, electrically, magnetically, mechanically, or the like.

Transform—to change one or more values, and/or the number, of signals of a data set using one or more mathematical and/or logical operations. Transformation of a set of signals may produce a transformed set of the signals by changing values of one or more of the signals and/or by deleting/invalidating any suitable subset of the signals. Signal transformation may include reducing signal variation, deleting/invalidating outlier signals, subtracting a baseline value from signals, reducing the frequency of outliers, reducing the overlap of distributions of positive and negative droplet signals, modifying signals according to a regression line, assigning new values to signals based on comparing signal values to a threshold or range, or any combination thereof, among others.

Run—an operating period during which a set of droplets, generally droplets of about the same size and including partitions a sample, are tested.

Oligonucleotide—a nucleic acid of less than about one-hundred nucleotides.

Exogenous—originating externally. For example, a nucleic acid exogenous to a sample is external to the sample as originally isolated. As another example, a nucleic acid exogenous to an organism or cell is not native to the organism or cell, such as a nucleic acid introduced into the organism or cell by infection or transfection.

Endogenous—originating internally, such as present in a sample as originally isolated or native to a cell or organism.

II. System Overview

FIG. 3 shows a flowchart illustrating an exemplary method 5640 of performing a droplet-based assay. The steps shown for the method may be performed in any suitable order and in any suitable combination, including combination with any other steps or features presented elsewhere in the present disclosure.

A sample for the assay may be prepared, indicated at 5642. The sample may be an aqueous sample and may contain at least one analyte to be tested in the assay. Preparation of the sample may include combining the sample, and particularly the analyte thereof, with one or more reagents, to create a reaction mixture. The reaction mixture may, for example, be an amplification mixture, such as a PCR composition.

Droplets may be generated, indicated at 5644. The sample and/or reaction mixture may be partitioned into the droplets. Accordingly, the sample and/or reaction mixture may be disposed in the droplets and/or contained by the droplets upon droplet generation. The sample may be partitioned to form a set of droplets with at least one or a plurality of the droplets having no copies of the analyte and/or at least one or a plurality of the droplets having only one copy of the analyte.

Generation of droplets may be performed by one or more droplet generators that each create droplets serially, or droplets may be produced in bulk, such as by agitation (e.g., sonication, blending, stirring, shaking, or the like). The droplets may be monodisperse or polydisperse. The droplets may be aqueous droplets disposed in a nonaqueous continuous phase (e.g., an oil phase). The droplets and/or the continuous phase may include a surfactant.

A reaction may be performed, indicated at 5646. The reaction may be performed in any of the droplets that are competent for the reaction. Stated differently, the droplets may be reacted, which means that droplets may be subjected to one or more conditions that promote occurrence of a reaction in the droplets. The reaction may, for example, occur preferentially or at least substantially exclusively in droplets that contain the analyte.

Any suitable reaction may be performed in droplets. The reaction may be a binding reaction, a chemical reaction, or a combination thereof, among others. The reaction may amplify at least one nucleic acid target, which may be the analyte(s) itself or a surrogate therefor. In some cases, the reaction may be performed by heating the droplets, such that they are incubated at an elevated temperature (above room temperature). For example, the reaction may be performed by thermally cycling the droplets (i.e., heating and cooling the droplets, and/or an emulsion in which the droplets are disposed, multiple times to execute a plurality of heating and cooling cycles). Thermal cycling may promote nucleic acid amplification, such as by PCR or the ligase chain reaction, among others. Thermal cycling may be achieved by moving the droplets through distinct temperature zones, such as with the droplets disposed in a continuous phase flowing along a channel that traverses the temperature zones. Alternatively, thermal cycling may be achieved with the droplets disposed in an emulsion held by a container, with emulsion not flowing and with the temperature of the container (and the emulsion therein) varied over time by heating and cooling.

A signal may be detected, indicated at 5648. The signal may be detected from an emulsion including the droplets and a continuous phase. The signal may be detected from any suitable number of droplets according to a desired accuracy and confidence for an assay. For example, an assay may detect a signal from at least about $10^2$, $10^3$, $10^4$, or $10^5$ droplets, among others. Signal detection may be performed while the droplets are moving, such as traveling through a detection region (e.g., past a detection window) of a detector. The signal thus may be detected serially from the droplets. In some cases, the droplets may be carried to the detection region in a continuous phase that is flowing with the droplets through the detection region. The signal may be detected continuously from fluid (continuous phase plus droplets) or may be detected intermittently. If detected intermittently, the signal from a droplet may be detected at any suitable sampling frequency. In some cases, the signal may be detected as one or more images of droplets, such as an array of droplets in an emulsion. Accordingly, the signal may be detected from a plurality of the droplets concurrently and/or while the plurality of droplets are at least generally motionless.

The detected signal may be detected optically by measuring light, also termed optical radiation (i.e., ultraviolet light, visible light, and/or infrared light). For example, the signal may be a fluorescence signal. If two or more different fluorescence signals are measured from each droplet, the signals may, for example, be detected at distinct wavelengths or wavebands. Alternatively, the fluorescence signals may be measured at the same wavelength/waveband after excitation with different wavelengths or wavebands of light (e.g., excitation at different times or at different positions), among others. Two or more fluorescence signals may be detected from respective distinct fluorophores.

An aspect of an analyte may be determined, indicated at 5650. The aspect may be determined based on the signal(s) detected. The aspect may, for example, be a concentration, an activity, a conformation, an association, a modification, etc. The aspect may be in relation to the droplets and/or the sample. If a concentration is determined, the concentration may, for example, be expressed as molecules/copies per droplet, molecules/copies/moles per unit volume of sample, molecules/copies/moles in the original sample, or the like.

FIG. 4 shows a flowchart illustrating an exemplary method 5660 of determining a concentration of an analyte based on at least one detected signal, which may be performed as step 5650 of method 5640 of FIG. 3. The steps of method 5650 may be performed in any suitable order and in any suitable combination, including combination with any other steps or features presented elsewhere in the present disclosure.

Droplet signals may be found, indicated at 5662. In other words, a droplet- or peak-finding algorithm may be utilized to identify portions (e.g., peaks) of the signal detected from an emulsion or continuous phase and representing individual droplets within the emulsion or continuous phase. The droplet-finding algorithm may identify droplet signals according to any suitable criteria, such as comparing a signal from a peak with one or more predefined conditions for peak height, peak shape, peak width, or a combination thereof, among others. In some cases, each droplet signal may be identified by comparing the detected signal with one or more thresholds (e.g., using a signal characteristic described above for the positive/negative threshold). For example, the maximum or total intensity of the signal (e.g., the peak height or peak area) from a negative droplet may be compared with a threshold value, to distinguish the droplet from noise (e.g., see Example 2). The algorithm may be capable of identifying a droplet signal for each droplet (e.g., without distinguishing whether the droplet is positive or negative) or only for droplets that produce a stronger signal (e.g., positive droplets only or positive droplets and only a subset of negative droplets).

Positive droplets may be identified, indicated at 5664. Droplets that test positive for a reaction (and thus for the presence of the analyte or target) may be identified by comparing each droplet signal identified (from 5662) with a predefined condition, such as a threshold, that distinguishes positive droplets from negative droplets. For example, the maximum intensity (and/or the peak height) of the droplet signal detected from a droplet may be compared with a threshold (also termed a threshold value), to classify the droplet as positive or negative. In other examples, the signal for a droplet may be integrated, averaged, smoothed, and/or the like, and then compared with one or more predefined conditions (e.g., one or more thresholds) to distinguish positive droplets from negative droplets.

Positive droplets may be counted, indicated as 5666. More particularly, droplet signals identified as corresponding to positive droplets may be counted to determine how many droplets from the complete set analyzed test positive for a reaction and/or a target, among others. In some cases, counting positive droplets may find the number of droplets analyzed that contain an analyte/target molecule. In some cases, negative droplets (i.e., droplets that are non-positive and not excluded) may be counted instead of positive droplets, because either the number of positive droplets or the number of negative droplets may be used for subsequent steps.

The total number of droplets may be determined, indicated at 5668. The total number represents both the positive (or negative) droplets that were counted at 5666 and negative (or positive) droplets that were not counted. The total number of droplets may be determined by counting both negative droplets and positive droplets, if droplet signals for both types of droplets were identified efficiently at 5662. Alternatively, the total number of droplets may be estimated. Further aspects of determining the total number of droplets by counting peaks and by estimation are described below in Example 2.

A fraction of the total number of droplets that are positive, or a fraction that are negative, may be calculated, indicated at 5670. The fraction may be calculated as the number of counted positive (or negative) droplets (at 5666) divided by the total number of droplets determined (at 5668). Alternatively, a negative (or positive) fraction may be calculated as the number of counted negative (or positive) droplets divided by the total number of droplets determined, and then the positive (or negative) fraction can be calculated as one minus the negative (or positive) fraction.

The concentration of the analyte may be obtained, indicated at 5672. The concentration may be expressed with respect to the droplets and/or with respect to a sample disposed in the droplets and serving as the source of the analyte. The concentration of the analyte in the droplets may be calculated from the fraction of positive (or negative) droplets by assuming that analyte molecules have a Poisson distribution among all of the droplets. With this assumption, the fraction f(k) of droplets having k copies of the analyte is given by the following equation:

$$f(k) = (C^k/k!)\exp(-C)$$

Here, C is the concentration of analyte in the droplets, expressed as the average number of analyte copies/molecules per droplet. Simplified Poisson equations may be derived from the more general equation above and used to determine analyte concentration from the fraction of positive (or negative) droplets. An exemplary Poisson equation that may be used is as follows:

$$C = -\ln(1-f_p)$$

where $f_p$ is the fraction of positive droplets (i.e., $f_p = f(1)+f(2)+f(3)+\ldots$), which is a measured estimate of the probability of a droplet having at least one copy of the analyte. Another exemplary Poisson equation that may be used is as follows:

$$C = -\ln(f_n)$$

where $f_n$ is the fraction of negative droplets (or $1-f_p$), which is a measured estimate of the probability of a droplet having no copies of the analyte, and C is the concentration as described above.

In some embodiments, an estimate of the concentration of the analyte may be obtained directly from the positive fraction, without use of a Poisson equation. In particular, the positive fraction and the concentration converge as the concentration decreases. For example, with a positive fraction of 0.1, the concentration is determined with the above equation to be about 0.105, a difference of only 5%; with a positive fraction of 0.01, the concentration is determined to be about 0.01005, a ten-fold smaller difference of only 0.5%. However, use of the Poisson equation can provide a more accurate estimate of concentration, particularly with a relatively higher positive fraction, because the equation accounts for the occurrence of multiple analyte copies/molecules per droplet.

FIG. 5 shows an exemplary system 5740 for performing droplet-based tests of nucleic acid amplification with the aid of controls and/or calibrations. System 5740 may include any combination of a sample/reagent storage/preparation assembly 5742, at least one droplet generator 5744, an amplification assembly, such as a thermal cycler 5746, a detection assembly 5748, and a controller 5750 incorporating a data analyzer 5752 and a feedback and control portion 5754, among others.

The system may provide at least one flow stream that carries at least one sample and reagents from one or more upstream positions and in a downstream direction to detection assembly 5748. Signals detected from the flow stream, and particularly droplet signals, may be communicated to data analyzer 5752. The data analyzer may analyze the signals to determine one or more test results, control results, calibration results, a quality (e.g., validity, reliability, confidence interval, etc.) of any of the results, or a combination thereof. Any of the results may be communicated to feedback and control portion 5754, which may control and/or adjust control of any of storage/preparation assembly 5742, droplet generator 5744, thermal cycler 5746, detection assembly 5748, and data analyzer 5752, based on the results determined.

Storage/preparation assembly 5742 may contain and/or supply at least one sample 5756, at least one set of test reagents 5758 (also termed target reagents), one or more control reagents 5760, one or more calibration reagents 5762, or any combination thereof. Any of the samples and/or reagents may be stored and/or supplied separately, may be stored and/or supplied as one or more pre-formed mixtures, and/or may be mixed selectably before they are supplied to a downstream region of the system (e.g., droplet generator 5744, thermal cycler 5746, or detection assembly 5748). Furthermore, any of the samples and/or reagents may travel sequentially from storage/preparation assembly 5742 to droplet generator 5744, thermal cycler 5746, and then detection assembly 5748 for detection of droplet signals. Alternatively, any of the samples and/or reagents may reach the detection assembly without travel through the droplet generator, as indicated at 5764, the thermal cycler, or both, as indicated at 5766. Accordingly, any of the samples and/or reagents disclosed herein may be stored and/or supplied in pre-formed droplets. Droplets may, for example, be pre-formed off-line, either locally or remotely. Pre-formed droplets may be intermixed randomly with droplets formed by droplet generator 5744 before reaching detection assembly 5748, or distinct types of droplets may be detected as spatially and/or temporally separated sets of droplets.

Test reagents 5758 are any reagents used to test for amplification of one or more targets, such as one or more primary targets, in partitions of a sample. Primary targets generally comprise any targets that are of primary interest in a test. Primary targets may be present at an unknown level in a sample, prior to performing tests on the sample. Test reagents 5758 generally include one or more sets of target reagents conferring specificity for amplification of one or more particular nucleic acid targets to be tested in a sample. Thus, the test reagents may include at least one pair (or two or more pairs) of primers capable of priming amplification of at least one (or two or more) nucleic acid target(s). The test reagents also may comprise at least one reporter to facilitate detecting amplification of each test target, a polymerase (e.g., a heat stable polymerase), dNTPs, and/or the like. The test reagents enable detection of test signals from droplets.

Control reagents 5760 are any reagents used to control for test signal variation (generally, variation other than that produced by differences in amplification) and/or to interpret results obtained with the test reagents (such as a reliability and/or validity of the results). The control reagents permit control signals and/or reference signals to be detected from droplets, either the same or different droplets from the test signals. Control reagents may be mixed with test reagents prior to droplet formation and/or control droplets containing control reagents may be produced separately from the test droplets and introduced independently of the sample.

The control reagents may provide instrument controls, that is, controls for variation introduced by the system (and/or its environment). Thus, instrument controls may control for variation in droplet volume, droplet detection efficiency, detector drift, and the like. Reference signals may be detected from droplets containing control reagents that function as instrument controls.

The control reagents also or alternatively may provide amplification controls, that is, controls that test for secondary/control amplification in droplets. The control reagents thus may include reagents used to test for amplification of at least one secondary or control target in droplets. The secondary/control target may be of secondary interest in a test, and/or may be present at a known or expected level in the sample, among others. In any event, the control reagents may include one or more sets of target reagents conferring specificity for amplification of one or more control nucleic acid targets to be tested in droplets. The control reagents may include at least one pair (or two or more pairs) of primers capable of priming amplification of at least one (or two or more) control nucleic acid target(s). The control reagents also may comprise at least one reporter to facilitate detecting amplification of each control target, a polymerase (e.g., a heat stable polymerase), dNTPs, and/or the like, or any suitable combination of these control reagents may be supplied by the test reagents. Control signals may be detected from control reagents that function as amplification controls.

Calibration reagents 5762 are any reagents used to calibrate system operation and response. Droplets containing a calibration reagent (i.e., calibration droplets) may be introduced into a flow stream of the system, at any position upstream of the detection assembly, for the purpose of calibrating the system (e.g., calibrating flow rates, excitation power, optical alignment, detector voltage, amplifier gain, droplet size, droplet spacing, etc.). Calibration droplets may be introduced into a flow stream of the system before, during, and/or after introduction of test droplets into the flow stream. In some embodiments, the level of a dye within control droplets may be used to calibrate and/or validate detector response, such as by using a pair of dye concentrations providing calibration signals that bracket an intended measuring range and/or that are disposed near upper and lower ends of the measuring range. For example, droplets of known size and containing one or more known dye concentrations may be prepared off-line and introduced into the system, and/or may be generated by the system. In some embodiments, calibration droplets may comprise fluorescent particles such as quantum dots, polymer beads, etc.

System 5740 may used to perform a method of analyzing one or more samples. The method may include any suitable combination of the steps disclosed herein, performed in any suitable order.

Droplets may be obtained. The droplets may be of one type or two or more types. At least a subset, or all, of the droplets may be generated by the system or may be pre-formed off-line. At least a subset of the droplets may include test reagents for testing amplification of a test nucleic acid target. At least a subset of the droplets may include control reagents and/or calibration reagents for testing amplification of a control nucleic acid target. The droplets may contain one or more dyes.

The droplets may be introduced into a flow stream upstream of a detector. All of the droplets may be introduced into the flow stream at the same position or the droplets, particularly droplets of different types, may be introduced at two or more distinct positions.

The droplets, in the flow stream, may be subjected to conditions that facilitate amplification. For example, the droplets may be heated and/or may be heated and cooled repeatedly (thermally cycled).

Signals may be detected from the droplets. The signals may include test signals, control signals, reference signals, calibration signals, or any combination thereof.

The signals may be analyzed. Analysis may include transforming test signals. Analysis also or alternatively may include comparing test signals and/or transformed test signals to a signal threshold to assign individual droplets as being positive or negative for amplification of a nucleic acid target. A number and/or fraction of target-positive droplets may be determined based on results of the comparison. Analysis further may include estimating a presence of a nucleic acid target in the sample. The estimated presence may be no target in the sample. Estimation of the presence may (or may not) be performed using Poisson statistics.

III. Exemplary Instrument Controls and Calibrators

FIG. 6 shows selected aspects of system 5740 in an exemplary configuration 5780 for detecting amplification of a nucleic acid target using a first dye and for controlling for system variation during a test using a second dye. In FIG. 6 and in other system configurations presented in succeeding figures of the present disclosure, the terms "droplet generator," "thermal cycler," and "detection assembly" are abbreviated "DG," "TC," and "DET."

Storage/preparation assembly 5742 may supply an amplification mixture to droplet generator 5744. The amplification mixture may incorporate a sample 5756, target reagents 5782 (i.e., test reagents 5758) including a first dye 5784 (dye 1), and a second dye 5786 (dye 2). The second dye and the target reagents may be mixed with one another before introduction into system 5740 or may be mixed within the system. Target reagents 5782 may provide primers for amplification of a nucleic acid target, and the first dye may enable detection of whether amplification occurred. The first and second dyes may be fluorescent dyes that are distinguishable optically. The second dye may be a passive reference or instrument control. In other words, the second dye may provide a detectable signal having an intensity that is at least substantially independent of the extent of amplification, if any, of any nucleic acid target. In some cases, the second dye may be a droplet marker for identification of droplet positions within a continuous phase.

Droplet generator 5744 may form droplets of the amplification mixture. The droplets may travel through thermal cycler 5746, to promote amplification of the nucleic acid target, if any, in each droplet. The droplets then may travel to detection assembly 5748. Assembly 5748 may detect, for each droplet, a test signal from the first dye and a reference signal (also termed a control signal) from the second dye.

FIG. 7 shows exemplary target reagents 5782 and a control reagent 5760 that may be included in system configuration 5780 of FIG. 6. The target and control reagents may permit detection of test signals in a first detection channel 5788 ("channel 1") and detection of reference signals in a second detection channel 5790 ("channel 2"). The first and second channels may represent distinct wavelengths and/or at least substantially nonoverlapping wavelength ranges.

Target reagents may include a reporter, such as a probe 5792, and target-specific forward and reverse primers 5794. Probe 5792 may be an energy transfer probe (e.g., a TAQMAN probe) including a nucleic acid, such as an oligonucleotide 5796, that binds to amplified target, and an energy transfer pair connected to strand 5796. The energy transfer pair may, for example, be formed by first dye 5784 and a quencher 5798.

Control reagent 5760 may include second dye 5786. The second dye may (or may not) be connected to a nucleic acid, such as an oligonucleotide 5800. Connection to the oligonucleotide may be covalent and/or through a binding interaction. Connection of the second dye to an oligonucleotide or other water-soluble molecule may improve retention of the second dye in the aqueous phase of a droplet and/or may facilitate distribution of the dye throughout the aqueous phase, among others.

FIG. 8 shows a flowchart illustrating of an exemplary approach to correcting for system variation using system configuration 5780 (FIG. 6), and, optionally, the reagents illustrated in FIG. 7. Test signals (i.e., target signals) and reference signals may be detected from the same droplets. For example, test signals may be detected in a first channel and reference signals may be detected in a second channel. Graphs illustrating coincident detection of test signals and reference signals are shown at 5810, 5812, respectively.

Test signal variation may introduce errors in data processing. For example, graph 5810 shows substantial variation in the intensity of the test signals detected. As a result, some of the test signals may be erroneously classified as positives or negatives. In the present illustration, two false positives are marked. However, variation of the test signals may be mirrored by variation of the reference signals detected from the same droplets. Accordingly, the test signals may be transformed based on the reference signals, indicated at 5814, to correct for variation in the test signals, as shown in a graph 5816, which plots the transformed test signals. The test signals may be transformed by any suitable operation or set of operation involving the reference signals. For example, the test signals may be transformed through dividing test signals by reference signals, such as dividing each test signal by its corresponding reference signal, which may be described as normalizing the test signals. Alternatively, the test signals may be transformed based on the reference signals by, for example, baseline subtraction, distance from the regression line, or the like. A transformation may compensate for variations in the test channel. This compensation or correction may make the test signals (i.e., negative test signals and/or positive test signals) more uniform in value and/or more Gaussian. The transformation also or alternatively may reduce the frequency of outliers and/or the overlap of the distributions of positive and negative signals.

FIG. 9 shows selected aspects of system 5740 in an exemplary configuration 5830 for (a) detecting amplification of a nucleic acid target in a set of droplets and (b) system calibration and/or correction for system variation in another set of droplets. Configuration 5830 is similar to configuration 5780 of FIG. 6, except that target reagents 5782 and control reagent 5760 are not in the same droplets. Accordingly, the target reagents and the control reagent may be supplied to respective distinct droplet generators of the system, indicated at 5832, may be supplied to the sample droplet generator at different times, or the control reagent may be supplied in pre-formed droplets that do not pass through the droplet generator, indicated at 5834, 5836. Since the target reagents and the control reagent are not in the same droplets in this configuration, the control reagent may include the same dye as the target reagent (i.e., first dye 5784) or may include a distinct dye (such as second dye 5786).

Figure 10:
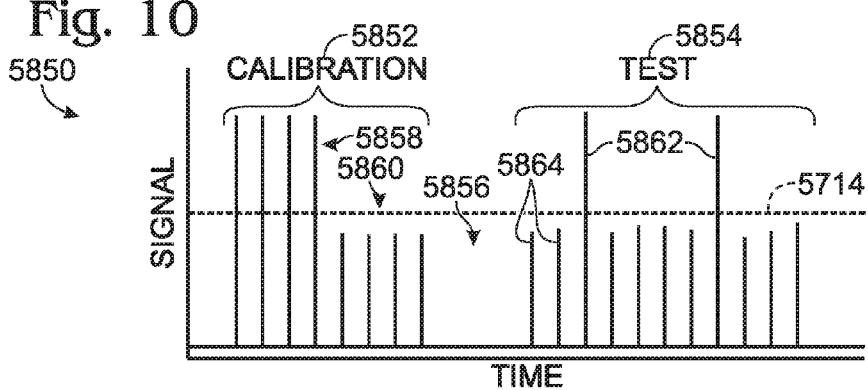
FIG. 10 is an exemplary graph of fluorescence signals that may be detected over time from a flow stream of the system configuration of FIG. 9 during system calibration and sample testing performed serially, in accordance with aspects of present disclosure.

FIG. 10 shows an exemplary graph 5850 of fluorescence signals that may be detected over time from a flow stream of system configuration 5830 (FIG. 9) during system calibration, indicated at 5852, and sample testing, indicated at 5854. Calibration and sample testing may be performed without or with mixing of calibration and test droplets.

Calibration and sample testing may be performed serially, without mixing of droplet types, using the same dye (and/or detection of the same wavelength(s)). By keeping calibration and test droplets separate, the distributions of test and calibration signal intensities may overlap. For example, calibration droplets and test droplets may be separated temporally in the flow stream, such that each type of droplet is identifiable based on its time of arrival at the detection assembly. The time of arrival may be calculated based on the relative time of introduction of each droplet type into the flow stream and the velocity of the flow stream. Thus, the calibration and test droplets may not (or may) be distinguishable based on signal intensity, but may be distinguishable temporally. In particular, the test and calibration droplets may be separated by a temporal (and spatial) gap 5856, which may identify a transition between droplet types. The use of temporal gaps also may permit introduction of a set of calibration droplets within a set of test droplets (i.e., within a test run), with a gap preceding and following the set of calibration droplets, to provide identification of each transition to a different droplet type. Stated differently, calibration may be performed during sample testing, by inserting calibration droplets into a train of test droplets, such that the train of test droplets is divided into two or more discrete groups.

Calibration droplets may include two or more types of droplet, which may be introduced separately or intermixed. For example, FIG. 10 shows a set of stronger calibration signals 5858 followed by a set of weaker calibration signals 5860 produced by distinct types of calibration droplets. Stronger and weaker calibration signals 5858, 5860 may correspond generally in intensity to respective positive test signals 5862 and negative test signals 5864. In other embodiments, only one type or three or more types of calibration droplet may be used, and may be configured respectively to provide one or three or more intensities of calibration signals.

Calibration and sample testing alternatively may be performed with calibration and test droplets randomly intermixed and thus not distinguishable temporally. Intermixed calibration and test droplets may be distinguishable by incorporating distinguishable dyes into the respective droplet types and, optionally, by detection of the distinguishable dyes at respective distinct wavelengths. Alternatively, or in addition, calibration droplets and test droplets may be distinguishable according to signal intensity detected at the same wavelength(s) and optionally from the same dye. In particular, calibration droplets may be designed to have one or more signal intensities outside the signal range of test droplets (i.e., the signal range provided by the collective distribution of signal intensities from negative and positive test droplets (e.g., see FIG. 2)). Thus, calibration droplets may be identified based on their calibration signals having signal intensities above and/or below the signal range of test droplets.

Figure 11:
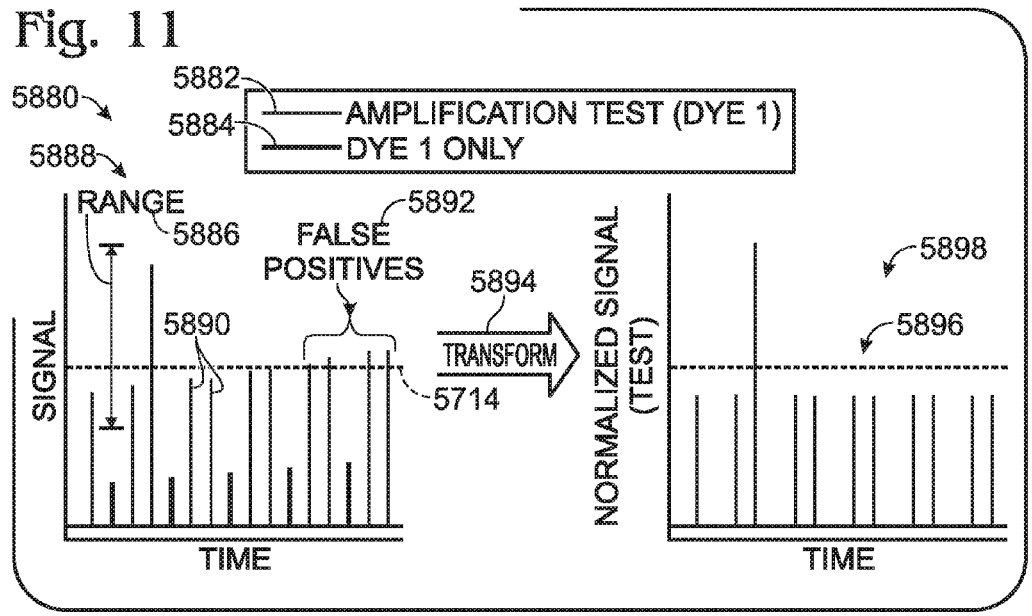
FIG. 11 is a flowchart of an exemplary method of correcting for system variation produced during a test using the system configuration of FIG. 9, in accordance with aspects of the present disclosure.

FIG. 11 shows a flowchart 5880 of an exemplary approach to correcting for signal variation during an amplification test using system configuration 5830 of FIG. 9. The approach illustrated in FIG. 11 distinguishes types of droplet signals, namely, test droplet signals 5882 and reference droplet signals 5884, based on differences in signal intensity detected in the same detection channel, as described above for calibration droplets. In particular, test droplets may produce a range 5886 of signal intensities, and reference signals 5884 may have intensities below (or above) the range. Accordingly, the distinct types of droplets may be interspersed randomly in the flow stream.

The reference droplets may be formed with the same amount (or two or more discrete amounts) of dye. Accordingly, without signal variation generated by the system, the reference droplets should produce reference signals of the same intensity. Variation in reference signal intensity may be mirrored by corresponding changes in the intensity of test signals. For example, in graph 5888, the intensity of reference signals 5884 and negative test signals 5890 show a gradual increase with respect to time. As a result, test signals from amplification-negative droplets may produce false positives 5892.

Variation in test signals 5882 may be reduced by transforming the test signals, indicated at 5894, based on reference signals 5884, to produce normalized test signals 5896 presented in graph 5898. Transformation may, for example, be performed by transforming each test signal based on one or more reference signals temporally proximate to the test signal, a weighted average of reference signals temporally proximate to the test signal, a sliding window of averaged reference signals that overlaps the test signal, or the like. Transformation before comparing test signals to a threshold may reduce the incidence of false positives, as shown here, the incidence of false negatives, or both.

IV. Exemplary Amplification Controls

Figure 12:
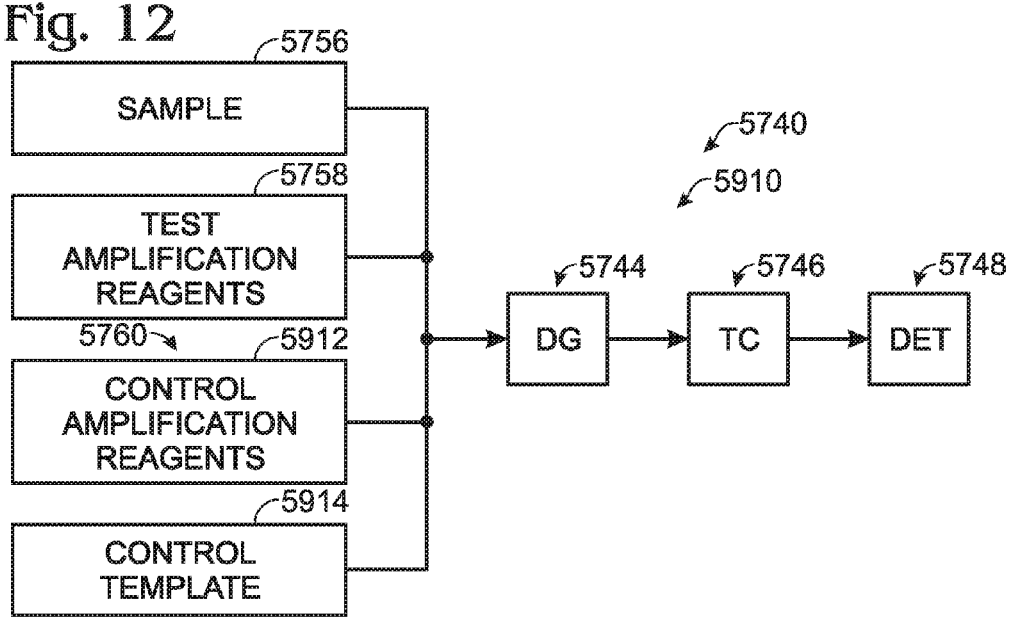
FIG. 12 is a schematic view of selected aspects of the system of FIG. 5, with the system in an exemplary configuration for testing amplification of a pair of nucleic acid targets in the same droplets, in accordance with aspects of present disclosure.

FIG. 12 show selected aspects of system 5740 of FIG. 5, with the system in an exemplary configuration 5910 for testing amplification of at least a pair of nucleic acid targets in the same droplets. System configuration 5910 may form an amplification mixture, which is supplied to droplet generator 5744. The amplification mixture may incorporate a sample 5756, test amplification reagents 5858, control amplification reagents 5912, and at least one control template 5914. Any combination of the sample, test reagents, control reagents, and control template may be mixed with one other before introduction into system 5740, or may be mixed within the system. Test reagents 5758 and control reagents 5912 may provide primers for respective amplification of at least one test target and at least one control target.

Amplification of the test and control targets may, for example, be detected via a first dye and a second dye, respectively, which may be included in respective first and second reporters (e.g., first and second probes). Signals from the first and second dyes may be detected in distinct (e.g., at least substantially nonoverlapping) first and second channels (i.e., a test channel and a control channel) as test signals and control signals, respectively.

Control template 5914 may comprise exogenous molecules of the control target. In contrast, the sample may be tested for a presence of endogenous molecules of the test target. The control template 5914 may be present in any suitable amount to provide any suitable average number of control template molecules per droplet, to generate a desired fraction of droplets positive for the control template. For example, the number of template molecules provided by template 5914 may be substantially less than an average of one per droplet, such as an average of about 0.1, 0.05, 0.02, or 0.01 molecule per droplet. Accordingly, the number/concentration of control template molecules may be selected such that the frequency of amplification of both test and control targets in the same droplet is low, which may minimize competition that may be caused by amplification of both test and control targets. For example, the control template may be present in no more than about one in five droplets.

The frequency of amplification of the control target may be determined by performing an analysis with the system. In some embodiments, this frequency may be compared with one or more previously determined frequencies of amplification for the control target and/or may be compared with an expected value for the frequency provided by a manufacturer. In any event, a control value may be determined, with the control value corresponding to a number and/or fraction of the droplets that are amplification-positive for the control nucleic acid target.

Control signals acquired in the control channel may be used to measure and/or verify the quantitative accuracy of a run and/or the measurement precision of the system during two or more runs. The control signals also or alternatively may be used to interpret a test result, such as the quality of test data measured from a sample, for example, to verify the quantitative accuracy of the test data and/or to determine the validity and/or reliability of the test data. The test result may be interpreted based on control value determined. For example, the test result may be determined as being invalid if the control value is less than a threshold value. Furthermore, data acquired from the control channel, such as signals from amplification-negative control droplets, may provide reference signals, as described above in relation to FIG. 8. In other words, test signals may be transformed using control signals that functions as reference signals, to normalize the test signals.

Figure 13:
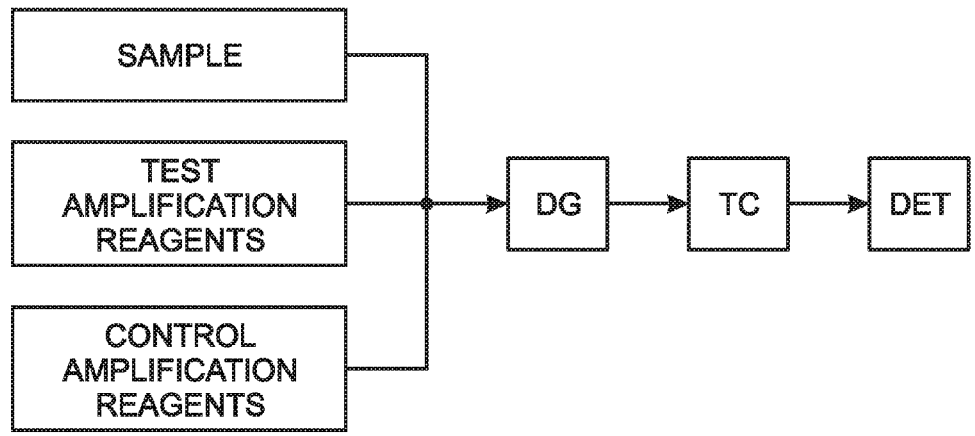
FIG. 13 is a schematic view of selected aspects of the system of FIG. 5, with the system in another exemplary configuration for testing amplification of a pair of nucleic acid targets in the same droplets, in accordance with aspects of present disclosure.

FIG. 13 shows selected aspects of system 5740 of FIG. 5, with the system in another exemplary configuration 5920 for testing amplification of at least a pair of nucleic acid targets in the same droplets. System configuration 5920 differs from configuration 5910 of FIG. 12 by including a different set of control amplification reagents 5922 (or a second set of test amplification reagents) and by the absence of an exogenous control template. Control reagents 5922 may amplify a control target that is known or expected to be present in sample 5756, and/or that has a known or expected representation with respect to a bulk nucleic acid population present in the sample (e.g., total DNA, total genomic DNA, genomic DNA from a particular species of organism, total RNA, total mRNA, etc.). In contrast, target reagents 5758 may amplify a test target that has an unknown presence in the sample and/or an unknown presence in with respect to the bulk nucleic acid population. In any event, amplification of the control target may be used to determine the quality of test data measured from a sample, such as to verify the quantitative accuracy of the test data and/or to determine the reliability of the test data. Furthermore, an amount of control target determined to be present in the sample may provide a standard against which an amount of test target determined to be present in the sample can be compared and/or normalized. In some embodiments, a control target is selected that is rare in the sample, such as a target representing a particular gene mutation. By selecting a rare control target, amplification of the control target can indicate the limit of detection of a test target and/or whether amplification of a low-abundance test target can occur. In some embodiments, the control target may be replaced by a second test target with an unknown presence in the sample (before testing).

Figure 14:
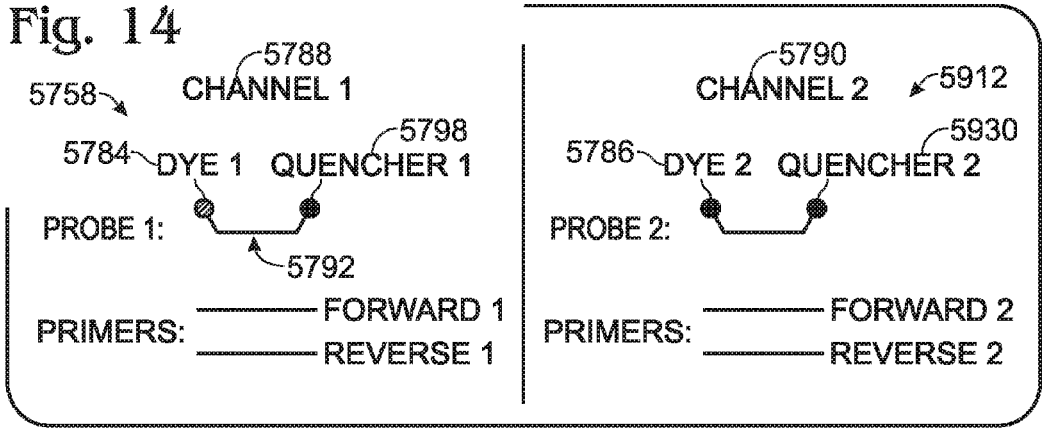
FIG. 14 is a schematic view of exemplary target-specific reagents that may be included in the system configurations of FIGS. 12 and 13, to permit detection of amplification signals in a different detection channel (i.e., a different detected wavelength or wavelength range) for each nucleic acid target, in accordance with aspects of present disclosure.

FIG. 14 shows exemplary test target reagents 5758 and control target reagents 5912 (or 5922) that may be included in system configuration 5910 (or 5920) of FIG. 12 (or 13), to permit detection of amplification signals in a different detection channel (i.e., channels 1 and 2, respectively) for each nucleic acid target. Test target reagents for channel 1 are described above in relation to FIG. 7. Control target reagents 5912 (or 5922) may be similar in general structure to the test target reagents, but different with respect to the nucleic acid sequences of the primers and probes, to provide test target and control target specificity, respectively. Also, the test and control probes may include distinct dyes 5784, 5786 and/or distinct energy transfer partners 5798, 5930 (e.g., distinct quenchers suitable for the respective dyes). In other embodiments, at least one of the probes may be replaced by a reporter including an intercalating dye, such as SYBR® Green.

FIGS. 15 and 16 show representative portions of exemplary data that may be obtained using system configuration 5910 or 5920 and the reagents of FIG. 14. The figures show exemplary graphs 5940-5946 of fluorescence signals that may be detected over time from a flow stream of the system using different detection channels, namely, a test channel (channel 1) that detects test data and a control channel (channel 2) that detects control data. In FIG. 15, graph 5940 of the test data contains no positive droplet signals. In contrast, graph 5942 of the control data identifies positive droplet signals, such as a positive signal 5948, at a frequency of about one in ten. Thus, the control data demonstrates that amplification in the droplets is not inhibited substantially and suggests that the lack of positive signals from the test data is due to an absence or undetectable level of the test target in the sample. Accordingly, the control data supports and helps to validate the negative result in the test data. In contrast, control graph 5946 of FIG. 16 shows no amplification of the control target (a substantially larger data set may be analyzed to demonstrate that the control result holds). The control data of graph 5946 thus indicates that amplification of the test target also is inhibited (or the sample is defective, such as too dilute (configuration 5920)), and that the negative test result is not valid.

FIG. 17 shows selected aspects of system of FIG. 5, with the system in an exemplary configuration 5960 for testing amplification of a pair of nucleic acid targets in respective different (i.e., nonoverlapping) sets of droplets. Configuration 5960 may be similar to that of configuration 5910, except that control reagents 5912 and control template 5914 are not mixed with sample 5756 and test target reagents 5758. Instead, droplets containing the control reagents and the control template may be formed separately in the system, indicated at 5962, or may be supplied as pre-formed droplets that are introduced into the flow stream downstream of droplet generator 5744, indicated at 5964.

Figure 18:
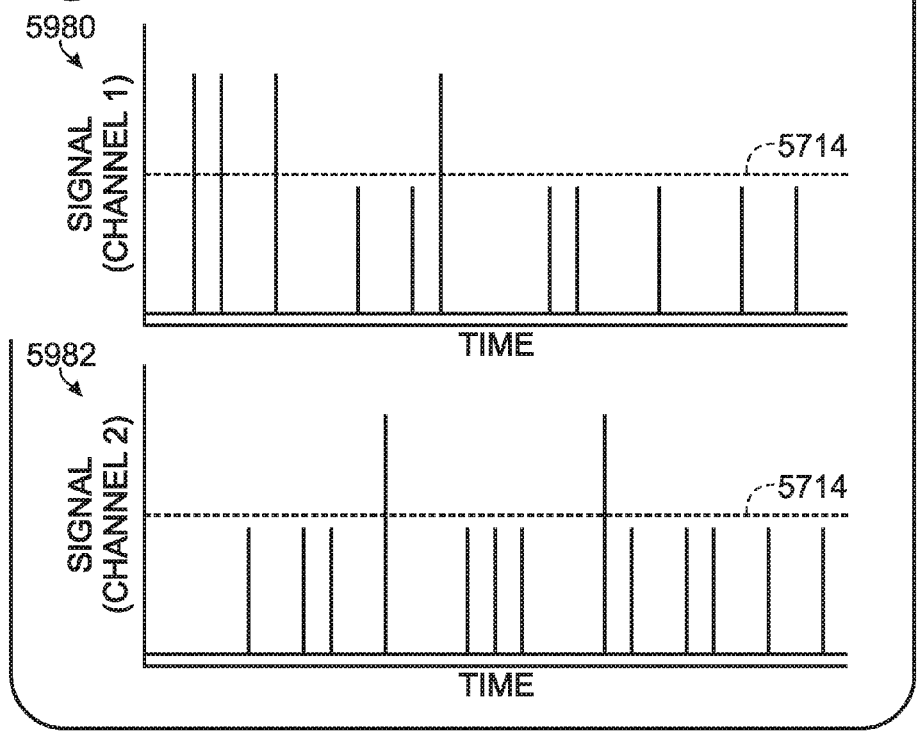
FIG. 18 is a pair of exemplary graphs of fluorescence signals that may be detected over time from a flow stream of the system configuration of FIG. 17 using different detection channels, with each channel monitoring amplification of a distinct nucleic acid target, in accordance with aspects of present disclosure.

FIG. 18 shows a pair of exemplary graphs 5980, 5982 of fluorescence signals that may be detected over time from a flow stream of system configuration 5960 of FIG. 17 using different detection channels. Graph 5980 plots fluorescence signals detected from a first channel, which detects amplification, if any, of a test target. Graph 5982 plots fluorescence signals detected from a second channel, which detects amplification, if any, of a control target. Successful amplification of the control target, as shown here, may, for example, verify and/or measure aspects of the system, such as operation of the thermal cycler and/or the detection assembly, the quality of the reagents, fraction of amplification-positive droplets, or any combination thereof, among others.

In configuration 5960, the test and control reagents are disposed separately in distinct droplets, so droplet signals in the first and second channels are not coincident, that is, they are not detected at the same time. In other embodiments, the control target may, instead, be a second test target and the control template may, instead, be another sample (or the same sample). Thus, the use of at least two detection channels permits droplets for distinct amplification tests to be interspersed in the flow stream.

V. Exemplary Multi-Channel Detection

Figure 19:
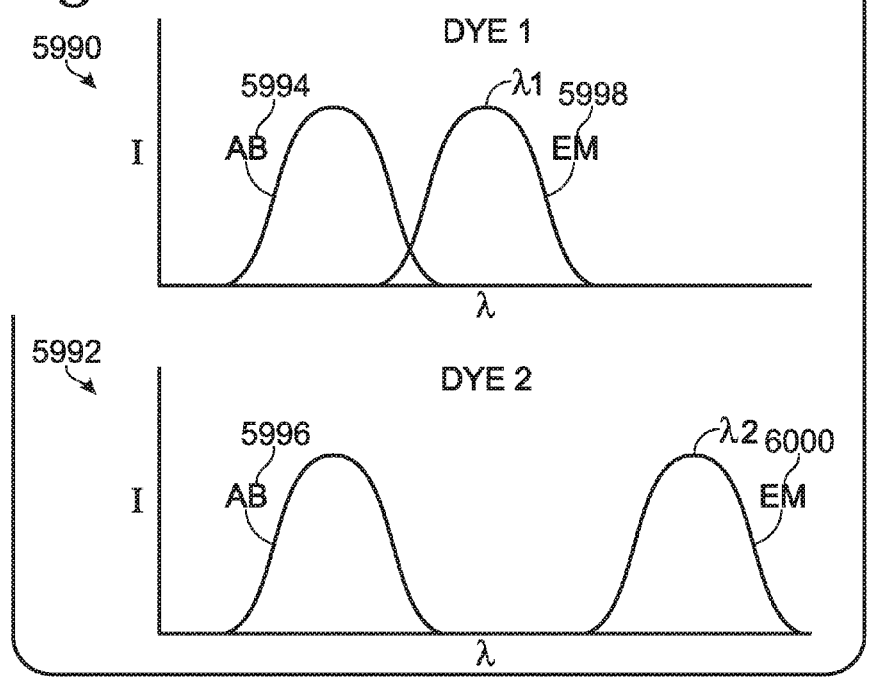
FIG. 19 is a pair of graphs illustrating exemplary absorption and emission spectra of fluorescent dyes that may be suitable for use in the system of FIG. 5, in accordance with aspects of the present disclosure.

FIG. 19 shows a pair of graphs 5990, 5992 illustrating exemplary absorption and emission spectra of fluorescent dyes that may be used in the system of FIG. 5. The dyes are arbitrarily labeled dye 1 and dye 2, respectively. However, either dye may be used to detect test signals or control signals in the various system configurations disclosed herein. Moreover, while illustrated here for two distinguishable dyes, the system may be used for detection and analysis with three, four, or more distinguishable dyes.

Each graph plots the intensity of absorption ("AB"), indicated at 5994, 5996, and emission ("EM"), indicated at 5998, 6000, for the corresponding dye. The dyes may have substantially overlapping absorption spectra, such that the same wavelength of light may be utilized to excite both dyes. In contrast, the dyes may exhibit Stokes shifts (i.e., the difference (in wavelength or frequency units) between the maxima of the absorption and emission spectra) of different magnitudes. For example, dye 1 may exhibit a smaller Stokes shift and dye 2 a larger Stokes shift, or vice versa. Accordingly, the emission spectra of the dyes may be substantially shifted with respect to one another. As a result, emission from the two dyes may be detected at least substantially independently of one another in different detection channels, such as a detection channel that detects light of a first wavelength or wavelength range (e.g., λ1) and another detection channel that detects light of a second wavelength or wavelength range (e.g., λ2).

Figure 20:
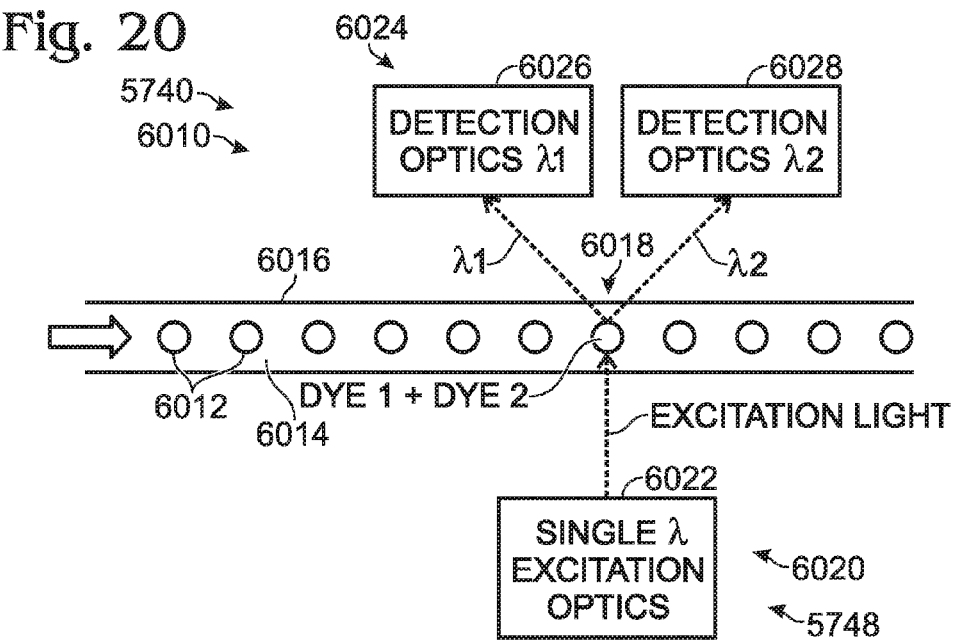
FIG. 20 is a schematic diagram illustrating exemplary use of the fluorescent dyes of FIG. 19 in an exemplary embodiment of the system of FIG. 5, in accordance with aspects of the present disclosure.

FIG. 20 is a schematic diagram illustrating exemplary use of the fluorescent dyes of FIG. 19 in an exemplary embodiment 6010 of system 5740 of FIG. 5. Droplets 6012 containing dyes 1 and 2, either in the same droplets or different sets of droplets, may be carried in a flow stream 6014 in a channel 6016. Flow stream 6014 may pass through a detection area 6018 established by an embodiment 6020 of detection assembly 5748.

Detection assembly 6020 may include a light source 6022 for exciting the fluorescent dyes in the droplets and at least one detector 6024 for detecting light emitted from the droplets. Light source 6022 may, for example, include an LED or laser that emits at least substantially a single wavelength of excitation light. Alternatively, or in addition, the light source may include at least one excitation optical filter that excludes other wavelengths of light emanating from the light source. Detector 6024 may be equipped with detection optics 6026, 6028 (e.g., beamsplitters, emission optical filters, separate detectors) that permit emitted light from the dyes to be detected separately.

Exemplary fluorescent dyes that may detected using system 6010 include a fluorescein derivative, such as carboxyfluorescein (FAM), and a PULSAR 650 dye (a derivative of Ru(bpy)$_3$). FAM has a relatively small Stokes shift, while PULSAR 650 dye has a very large Stokes shift. Both FAM and PULSAR 650 dye may be excited with light of approximately 460-480 nm. FAM emits light with a maximum of about 520 nm (and not substantially at 650 nm), while PULSAR 650 dye emits light with a maximum of about 650 nm (and not substantially at 520 nm). Carboxyfluorescein may be paired in a probe with, for example, BLACK HOLE Quencher™1 dye, and PULSAR 650 dye may be paired in a probe with, for example, BLACK HOLE Quencher™2 dye.

VI. Exemplary Self-Normalization of Droplet Signals

Test signals may be normalized using methods different from those described above in relation to FIGS. 8 and 11. In particular, the methods illustrated in FIGS. 8 and 11 involve transformation of test data with reference data detected (a) in a different detection channel (FIG. 8) or detected (b) in different droplets (FIG. 11). This section describes methods that transform test data using aspects of itself rather than another data set.

Figure 21:
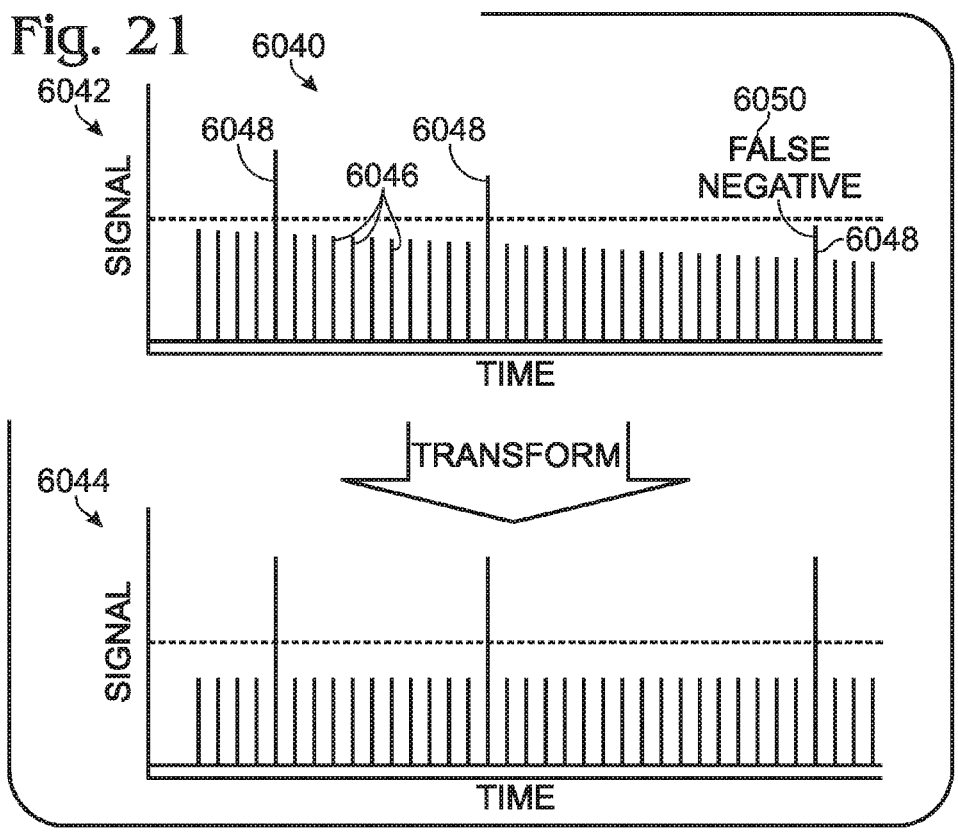
FIG. 21 is a flowchart of an exemplary approach to correcting for system variation within a test by processing a set of droplet test signals to a more uniform signal intensity, in accordance with aspects of the present disclosure.

FIG. 21 shows a flowchart 6040 illustrating an exemplary method of correcting for system fluctuations during a test. The method involves processing a set of droplet test signals, shown in a first graph 6042, to produce a transformed set of test signals, shown in a second graph 6044. Negative test signals 6046 and positive test signals 6048 each should have respective constant values over time if there is no system variation. However, system variation, such as the negative drift over time illustrated in graph 6042, may produce false negatives, such as a false negative signal 6050, and/or false positives. Transformation of the test signals may be performed to correct for system variation before the test signals are used to estimate a presence of a test target in sample being tested. In particular, individual test signals may be transformed differently using the test data, accordingly to the temporal position of each test signal. For example, each test signal may be transformed using temporally proximate test data, such as normalization of each test signal with respect to a sliding window that averages a subset of the test signals including or adjacent the test signal. The subset of the test signals used may be provisionally negative, positive, or negative plus positive test signals, any of which may be re-assigned as negative/positive after transformation. For example, graph 6044 shows re-assignment of false negative signal 6050 as positive after transformation.

Figure 22:
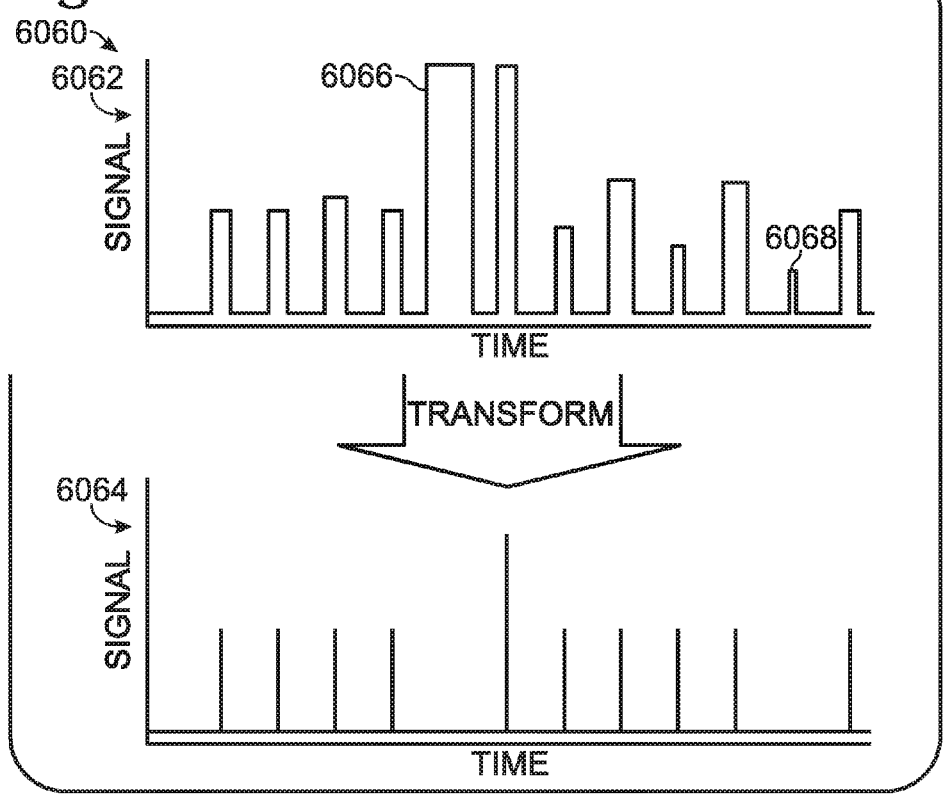
FIG. 22 is a flowchart of an exemplary approach for transforming droplet signals based on the width of respective signal peaks providing the droplet signals, in accordance with aspects of the present disclosure.

FIG. 22 shows a flowchart 6060 illustrating an exemplary method of transforming droplet signals based on the width of respective signal peaks providing the droplet signals. The flowchart involves graphs 6062, 6064, which represent test data before and after transformation, respectively.

Graph 6062 presents test data in which the width and height of each droplet peak is shown. (Here, each droplet peak is presented as a square wave to simplify the presentation. However, in other embodiments, each droplet peak may be detected as having any suitable shape, such as a wave with sloped leading and trailing sides.) The width of a droplet fluorescence peak may be used to determine the size and volume of each droplet, if droplet signals are detected in a flow stream with known flow rate, generally within a channel of fixed geometry. Knowing the volume of sample that is tested for amplification in droplets may be required for accurately determining the concentration/number of target molecules in the sample. If droplets of uniform size are desired, peak width may be used to identify droplets of sizes that are outside the desired range. For example, in FIG. 22, peaks 6066, 6068 having widths outside a predefined range are excluded from the data set. The droplet signals also may be transformed based on width, to provide transformed test data (i.e., graph 6064), that has been corrected for volume variation and/or variation in peak width.

VII. Examples

The following examples describe selected aspects and embodiments of the present disclosure, including exemplary methods of gating droplet data and of determining the total number of droplets. These examples are intended for illustration and should not limit the entire scope of the present disclosure.

Example 1

Exemplary Identification of Accepted and Rejected Droplets

Figure 23:
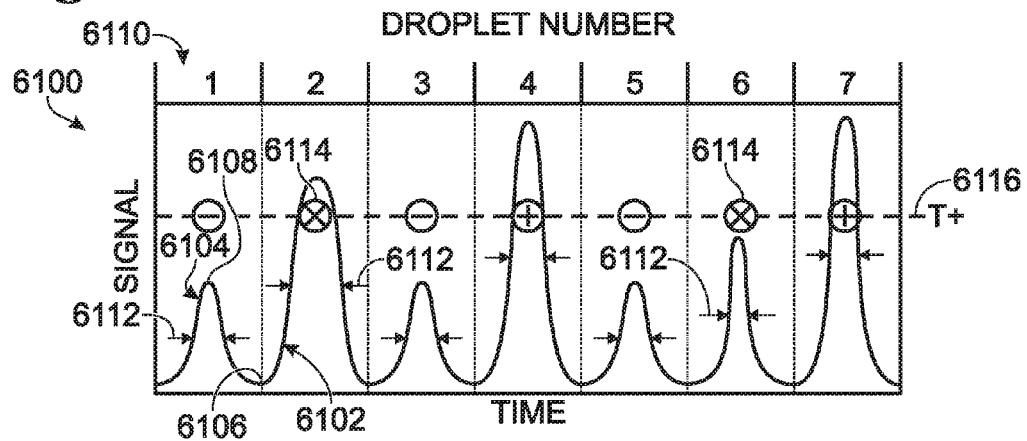
FIG. 23 is an exemplary graph of a signal that may be measured with respect to time from a fluid stream containing droplets, with individual peaks of the signal identified as positive droplets, negative droplets, or rejected droplets according to peak width and peak height, in accordance with aspects of the present disclosure.
Figure 24:
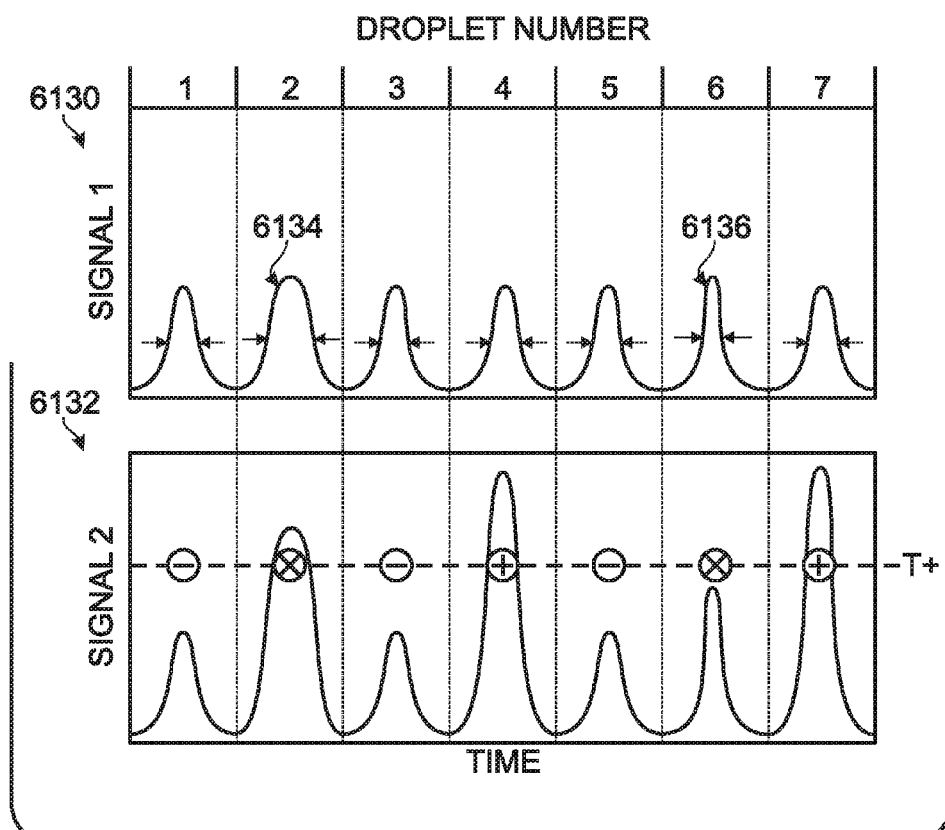
FIG. 24 is a pair of graphs of exemplary first and second signals that may be measured with respect to time from a fluid stream containing droplets, with individual peaks of the second signal identified as positive droplets, negative droplets, or rejected droplets according to peak width of the first signal and peak height of the second signal, in accordance with aspects of the present disclosure.

This example relates to culling data collected from droplets, as described above for FIG. 22; see FIGS. 23 and 24.

FIG. 23 shows an exemplary graph 6100 of a signal 6102 that may be measured with respect to time from a fluid stream containing droplets. In other embodiments, here and elsewhere in the present disclosure, the signal may be measured with respect to one or more spatial dimensions instead of time, such as when the signal is collected as an image of droplets. The signal may, for example, be generated by a fluorescence signal from an assay reporter (e.g., a probe) that reflects occurrence of a reaction, such as amplification of a nucleic acid target and/or other analyte.

Signal 6102 varies in strength over time as each droplet travels through a detection region where the signal is detected. In particular, the signal from each droplet (i.e., the "droplet signal") generates a wave or peak 6104 as the intensity of signal 6102 increases above a baseline 6106 to a maximum or crest 6108 and then returns back to the baseline. Here, the graph shows a series of seven peaks, which are labeled at 6110 as droplet numbers 1 to 7.

Each droplet signal or peak has a height, which is a measure of how far the peak extends above baseline 6106, and a width, which, in this case, relates to the time interval during which the peak is detected. The peak width corresponds to the size of the droplet, generally its diameter. In other cases, such as when droplets are imaged, the peak width also may correspond to droplet diameter. In any event, the peak width may be defined in any suitable manner, such as a width 6112 of the peak at one-half of the peak height.

The droplet signals may be gated to exclude peaks (and thus corresponding droplets) that do not meet one or more predefined conditions. Each peak (or droplet signal) may be compared with the predefined condition to identify the corresponding droplet as an accepted droplet (an included droplet), if the peak (or droplet signal) meets the predefined condition, or a rejected droplet (an excluded droplet), if the peak (or droplet signal) does not meet the predefined condition. For example, the predefined condition may be a permitted size (such as a range of sizes) for a droplet. The size of a droplet is generally related to a width (e.g., signal duration) and/or area (e.g., total signal) of a peak formed by the signal for the droplet. Accordingly, the size may, for example, be defined by the width of each peak, such as width 6112.

FIG. 23 shows droplet numbers 2 and 6, which are marked by a circled "X" at 6114, having widths 6112 that fall outside the permitted width (such as a range of widths) and thus are identified as excluded/rejected droplets. The remaining droplets (droplets 1, 3-5, and 7) are identified as included/accepted droplets. This gating process may be utilized to improve the monodispersity of droplets analyzed, by excluding data from droplets that fall outside of a permitted size (e.g., a predefined size range). Generally, more accurate results are provided by using data from droplets that are closer to the same size.

The droplet signal from each accepted droplet may be used to determine whether each accepted droplet is positive or negative for the presence of a target. The height of each peak may be compared with a positive threshold ("T+"), indicated by a dashed line at 6116. If the peak extends above the threshold line, the peak (and the corresponding droplet) is deemed positive (indicated by a circled "+" on the threshold line), and if not, the peak (and the corresponding droplet) is deemed negative (indicated by a circled "−" on the threshold line). The concentration of an analyte and/or target in the accepted droplets may be determined by selectively using data from the accepted droplets, that is, without any contribution of data from the rejected droplets.

The differences in height of positive and negative peaks may affect the width measured from each, independent of droplet size. Accordingly, it may be desirable to use a droplet marker and an assay reporter that generate respective, distinguishable signals (e.g., signals measured from different wavebands of light). The droplet marker may be used to size droplets for exclusion of droplets. A signal detected from the droplet marker may have a strength that corresponds to a size of each droplet. Also, the strength of the signal detected from the droplet marker may be at least substantially independent of whether or not the target is present in each droplet. The assay reporter may be used to distinguish positive from negative droplets for a reaction (and/or analyte/target). The strength of a signal detected from the assay reporter may vary according to whether or not a target is present in each droplet.

FIG. 24 shows a pair of graphs 6130, 6132 of exemplary first and second signals ("signal 1" and "signal 2") produced by a droplet marker and an assay reporter, respectively. The signals may be measured at respective distinct wavelength bands of light, which may or may not overlap. The droplet marker provides a peak size (such as height, width, and/or area, among others) for each droplet that corresponds to the droplet size. Accordingly, droplets having first-signal peaks that fail to meet a predefined condition (e.g., a permitted peak height, width, area, total signal, or the like) may be excluded from analysis of the corresponding second signal provided by the assay reporter. In other words, the first signal may be used to gate the second signal. Here, droplet numbers 2 and 6 generate first-signal peaks 6134, 6136 that fall outside a predefined peak width at half height. Accordingly, these droplets are identified as rejected droplets, as indicated by the circled "X" in graph 6132, and are not used to determine a concentration of a target. The remaining peaks produced by the second signal (graph 6132) may be used to identify positive and negative droplets and to obtain a concentration of a target, without any contribution of the second signal from the rejected droplets. For example, a fraction of the accepted droplets that are positive (or negative) may be used to calculate a concentration of the target in the accepted droplets, based on the target having a Poisson distribution among the accepted droplets.

Example 2

Exemplary Approaches to Determining Total Droplet Number

Signal peaks detected from negative droplets may be small and difficult to identify reliably. For example, an assay reporter with a low background (e.g., a fluorescent probe, such as a Taqman® probe) may produce a very weak signal (e.g., a strongly quenched signal) in the absence of reaction. Accordingly, counting the total number of peaks, and thus the total number of droplets analyzed, may not be practical with some assay reporters. This example describes exemplary approaches for determining the total number of droplets in an assay; see FIGS. 25-27.

FIG. 25 shows a graph 6150 of an exemplary signal 6152 that may be measured with respect to time from a fluid stream containing droplets. The signal may be produced by a reporter that is used to distinguish the presence or absence of at least one analyte or target molecule in individual droplets. A total of twelve equally spaced droplets produce signal 6152 presented in the graph. However, only three signal peaks 6154-6158 are identified reliably. Each peak exceeds a positive-droplet threshold 6160 ("T+"), and is identified as a positive droplet. The number of positive droplets may be counted, indicated at 6162.

In contrast, signal 6152 exhibits too much noise to provide reliable droplet identification with a droplet threshold 6164 ("Td"), because the droplet threshold must be set too close to the signal's baseline. Also, a bona fide peak 6166 detected from a droplet and a false peak 6168 produced by noise can be of comparable height.

The total number of droplets may be estimated, indicated at 6170, rather than counted. The estimate thus may be an external estimate. Estimation may be conducted by various strategies, generally without using the detected signal to perform the estimation and/or without counting all or any of the droplets. For example, the droplets may represent a known volume of an emulsion having an estimated or measured density of droplets in the known volume (i.e., the number of droplets per unit volume of the emulsion). Exemplary estimation of the density of droplets may be performed using, as a source of droplets, an emulsion containing packed droplets having a measured or assumed packing density. Alternatively, the droplets may be generated from a known total volume of aqueous phase and each may have a known average droplet volume, to permit the total number to be estimated by dividing the total volume by the average droplet volume. As another example, the droplets may be generated (and/or driven through a detection region) at a known rate for a known period of time, to permit the total number of droplets to be estimated by multiplying the rate by the period of time. In any event, the number of negative droplets may be determined by material balance: the counted number of positive droplets may be subtracted from the estimated total number of droplets to infer the number of negative droplets. For example, if it is estimated that there are 20,000 total droplets from which signal is detected, and 12,000 positive droplets are counted, then 8,000 of the droplets are inferred to be negative by material balance.

The concentration of an analyte or target in the droplets may be obtained from the counted number of positive droplets and the estimated number of total droplets. For example, a fraction of the total droplets that are positive (or negative) droplets may be calculated, and the fraction may be utilized to determine the analyte/target concentration based on the target/analyte having a Poisson distribution among the plurality of droplets.

FIG. 26 shows data that permit counting the total number of droplets. The data are collected from a set of twelve droplets each carrying a pair of distinguishable dyes, which create respective first and second signals detected from distinct wavebands of light. Graph 6150 (also see FIG. 25) is formed with first signal 6152, and second graph 6180 is formed with a second signal 6182. Signals detected over the same time interval are presented by the graphs.

Graph 6150 permits signal peaks 6154-6158 to be identified as positive droplets, as described above for FIG. 25. However, the assay reporter used to create first signal 6152 does not permit reliable identification of peaks for the other nine droplets (i.e., droplet numbers 1, 2, 4, 5, 7-9, 11, and 12). Accordingly, the total number of droplets cannot be counted accurately.

Graph 6180 presents second signal 6182 detected from a droplet marker present in each droplet. The droplet marker produces a distinct peak 6184 for every droplet, with the peak extending significantly above the signal baseline. According, a droplet threshold 6186 ("Td") may be set that accurately identifies at least substantially all bona fide peaks 6184 (and thus all of the droplets, whether positive or negative based on the first signal). The total number of droplets may be counted accurately using the second signal, and the number of positive droplets may be counted using the first signal. A fraction of the droplets that are positive (or a fraction that are negative) may be calculated and a concentration of the target obtained using Poisson statistics. In some cases, the total number of droplets may be determined by counting only a fraction (e.g., a contiguous fraction) of the droplets for only a portion of the total detection time, and then calculating the total droplet number by dividing the number counted by the fraction counted (e.g., as determined by dividing the counting time by the total detection time).

FIG. 27 shows data that permits counting the total number of droplets. However, in contrast, to the approach presented in FIG. 26, the same detected signal may be used for counting positive droplets and total (positive and negative) droplets. Here, the data is collected from a set of twelve droplets each carrying an assay reporter and a droplet marker. The assay reporter, if present without the marker, generates data presented in graph 6150 (also see FIG. 25). The droplet marker, if present without the reporter, generates data presented in a second graph 6190. Graph 6190 is similar to graph 6180 of FIG. 26, except that the signal from the droplet marker is not detected in a second channel. Accordingly, when the droplets carry both the assay reporter and the droplet marker, a combined signal 6192 is detected from the droplets as presented in a graph 6194 that corresponds to the sum of the signals from graphs 6150 and 6190.

The combined signal is composed of a first integral portion and a second integral portion. The first integral portion is produced by the assay reporter and has an intensity that varies according to whether or not a target is present in each droplet. The second integral portion is produced by the droplet marker and has an intensity that is at least substantially independent of whether or not the target is present in each droplet. The second integral portion may (or may not) be predominant over the first integral portion of the signal if the target is absent from a droplet. Alternatively, or in addition, the first integral portion of the signal may (or may not) be predominant over the second integral portion of the signal if the target is present in a droplet.

Combined signal 6192 permits identification and counting of each peak produced by the droplets (e.g., by comparing the peak height with droplet threshold 6186). The combined signal also permits identification and counting of each peak produced by a positive droplet (e.g., by comparing the peak height with positive-droplet threshold 6160).

The assay reporter and the droplet marker used to create combined signal 6192 both may include a fluorophore. The respective fluorophores may be excited by the same wavelength band of light and/or may emit light of overlapping (and/or the same) wavelength ranges. Accordingly, combined emission of light from the fluorophores may be detected from the same wavelength band. In some cases, the reporter and the marker may include the same fluorophore, with emission from the fluorophore of the reporter indicating whether a droplet is positive or negative and emission from the fluorophore of the marker being substantially independent of whether the droplet is positive or negative. In exemplary embodiments, the reporter is a probe that includes an oligonucleotide conjugated to a fluorophore, and the marker includes the fluorophore without the oligonucleotide (and/or without a quencher conjugated to the oligonucleotide).

Example 3

Selected Embodiments

This example describes selected embodiments of the present disclosure related to methods of using controls and calibrations for droplet-based assays, in accordance with aspects of the present disclosure, presented without limitation as a series of numbered paragraphs.

1. A method of performing a droplet-based assay, comprising: (A) detecting a first signal and a second signal from a plurality of droplets; (B) identifying accepted droplets of the plurality for which the first signal meets a predefined condition and rejected droplets of the plurality for which the first signal does not meet the predefined condition; and (C) determining a concentration of a target in the accepted droplets based on the second signal from the accepted droplets, and without any contribution of the second signal from the rejected droplets.

2. The method of paragraph 1, further comprising a step of amplifying the target in one or more of the plurality of droplets before the step of detecting.

3. The method of paragraph 2, wherein the step of amplifying the target includes a step of cycling the droplets thermally.

4. The method of any of paragraphs 1 to 3, wherein the step of detecting includes a step of detecting a first signal from droplets that are flowing.

5. The method of paragraph 4, wherein the step of detecting includes a step of detecting a first signal from droplets serially.

6. The method of any of paragraphs 1 to 3, wherein the step of detecting includes a step of detecting an image of droplets.

7. The method of any of paragraphs 1 to 6, wherein the predefined condition corresponds to a permitted size for the droplet.

8. The method of paragraph 7, wherein the permitted size corresponds to a permitted diameter for the droplets.

9. The method of any of paragraphs 1 to 8, wherein the first signal detected from each droplet forms a peak.

10. The method of paragraph 9, wherein the width of the peak is measured at about one-half of the peak height.

11. The method of paragraph 9, wherein the predefined condition is a permitted width of the peak.

12. The method of any of paragraphs 1 to 10, wherein the first signal is a fluorescence signal.

13. The method of paragraph 1, wherein the first signal has an intensity that corresponds to a size of each droplet and that is at least substantially independent of whether or not the target is present in the droplet.

14. The method of paragraph 1, wherein the step of determining includes a step of determining a fraction of the accepted droplets that are positive or a fraction that are negative for the target.

15. The method of paragraph 14, wherein the step of determining a fraction includes a step of counting droplets that are positive or that are negative for the target.

16. The method of paragraph 1, wherein the second signal has an intensity that varies according to whether or not the target is present in a droplet.

17. A method of performing a droplet-based assay, comprising: (A) generating a plurality of droplets containing an assay reporter and a droplet marker; (B) detecting from the plurality of droplets a signal representing combined emission of light from the assay reporter and the droplet marker, wherein the assay reporter provides a first integral portion of the signal having an intensity that varies according to whether or not a target is present in a droplet, and wherein the droplet marker provides a second integral portion of the signal having an intensity that is at least substantially independent of whether or not the target is present in a droplet; (C) counting a number of the plurality of droplets that are positive or that are negative for the target based on the signal; (D) determining a total number for the plurality of droplets based on the signal; and (E) obtaining a concentration of the target based on the counted number of droplets and the total number of droplets.

18. The method of paragraph 17, wherein the assay reporter and the droplet marker each include a same fluorophore.

19. The method of paragraph 17 or 18, wherein the assay reporter includes an oligonucleotide and a fluorophore.

20. The method of any of paragraphs 17 to 19, further comprising a step of illuminating droplets with electromagnetic radiation capable of producing the combined emission of light from the assay reporter and the droplet marker.

21. The method of any of paragraphs 17 to 20, wherein the droplet marker is selectively localized near or at a perimeter of each droplet.

22. The method of paragraph 21, wherein the droplet marker is selectively localized in or adjacent a skin that encapsulates the droplets.

23. The method of any of paragraphs 17 to 20, wherein the droplet marker is distributed at least substantially uniformly throughout each droplet.

24. The method of any of paragraphs 17 to 23, wherein the step of detecting includes a step of detecting a signal from droplets that are moving.

25. The method of any of paragraphs 17 to 24, wherein the step of detecting includes a step of detecting the signal from droplets serially.

26. The method of any of paragraphs 17 to 24, wherein the step of detecting includes a step of detecting an image of droplets.

27. The method of any of paragraphs 17 to 26, wherein the target is a nucleic acid target.

28. The method of any of paragraphs 17 to 27, wherein the step of obtaining includes a step of determining a fraction of the plurality of droplets that are positive or a fraction that are negative for the target.

29. The method of any of paragraphs 17 to 28, wherein the step of obtaining a concentration includes a step of determining a concentration of the target based on the target having a Poisson distribution in the plurality of droplets.

30. The method of any of paragraphs 17 to 29, further comprising a step of amplifying the target in one or more of the plurality of droplets before the step of detecting.

31. The method of paragraph 30, wherein the step of amplifying the target includes a step of cycling the plurality of droplets thermally.

32. The method of paragraph 17, wherein the second integral portion of the signal for a droplet is greater than the first integral portion of the signal for the droplet if the target is absent from the droplet.

33. The method of paragraph 17, wherein the first integral portion of the signal for a droplet is greater than the second integral portion of the signal for the droplet if the target is present in the droplet.

34. The method of paragraph 17, wherein the step of determining a total number includes a step of counting each droplet.

35. The method of paragraph 17, wherein the step of determining a total number includes a step of counting a portion of the plurality of droplets and a step of estimating the total number based on the portion counted.

36. The method of paragraph 17, wherein the light is visible light.

37. A method of performing a droplet-based assay, comprising: (A) detecting a signal from a plurality of droplets; (B) determining which of the droplets are positive for a target based on the signal; (C) counting the positive droplets to establish a number of positive droplets; (D) estimating a total number for the plurality of droplets; and (E) obtaining a concentration of the target based on the number of positive droplets and the total number of droplets.

38. The method of paragraph 37, wherein the signal is detected from droplets that are moving.

39. The method of paragraph 38, wherein the signal is detected serially from droplets flowing through a detection region.

40. The method of paragraph 37 or 38, wherein the step of detecting includes a step of detecting an image of droplets.

41. The method of any of paragraphs 37 to 40, wherein the signal is a fluorescence signal.

42. The method of any of paragraphs 37 to 41, wherein the target is a nucleic acid target.

43. The method of paragraph 42, further comprising a step of amplifying the nucleic acid target in one or more of the plurality of droplets before the step of detecting.

44. The method of paragraph 43, wherein the step of amplifying the nucleic acid target includes a step of cycling the droplets thermally.

45. The method of paragraph 37, wherein the step of estimating a total number is performed without use of the detected signal.

46. The method of paragraph 37, wherein the step of estimating a total number is performed without counting any droplets.

47. The method of paragraph 37, wherein the step of estimating a total number includes a step of counting a portion of the plurality of droplets before the step of detecting.

48. The method of paragraph 37, wherein the plurality of droplets are provided by a known volume of packed droplets, and wherein the step of estimating is based on the known volume and an estimated or measured packing density of droplets per unit volume in the packed droplets.

49. The method of paragraph 37, wherein the plurality of droplets are generated with a known total volume and have a known size, and wherein the step of estimating is based on the known total volume and the known size.

50. The method of paragraph 37, wherein the plurality of droplets are generated at a known rate for a known period of time, and wherein the step of estimating is based on the known generation rate and the known period of time.

51. The method of paragraph 37, wherein the step of obtaining includes a step of determining a fraction of droplets that are positive or a fraction that are negative for the target, and a step of finding a concentration of the target in the droplets based on the target having a Poisson distribution in the plurality of droplets.

52. A method of performing a droplet-based assay, comprising: (A) detecting a first signal from a plurality of droplets; (B) determining which of the droplets are positive for a target based on the first signal; (C) counting the positive droplets to establish a number of positive droplets; (D) detecting a second signal from the plurality of droplets, wherein the second signal has an intensity corresponding to a size of each droplet and substantially independent of whether or not the target is present in the droplet; (E) determining a total number for the plurality of droplets based on the second signal; and (F) obtaining a concentration of the target in the plurality of droplets based on the number of positive droplets and the total number of droplets.

53. The method of paragraph 52, wherein the first signal has an intensity that varies according to whether or not the target is present in a droplet.

54. The method of paragraph 52 or 53, wherein the step of detecting a first signal includes a step of detecting a first signal from droplets that are flowing.

55. The method of paragraph 54, wherein the step of detecting a first signal includes a step of detecting a first signal from droplets serially.

56. The method of any of paragraphs 52 to 54, wherein the step of detecting a first signal includes a step of detecting an image of droplets.

57. The method of any of paragraphs 52 to 56, wherein the first signal is a fluorescence signal.

58. The method of any of paragraphs 52 to 57, wherein the target is a nucleic acid target.

59. The method of paragraph 58, further comprising a step of amplifying the nucleic acid target in one or more of the plurality of droplets before the step of detecting.

60. The method of paragraph 59, wherein the step of amplifying the nucleic acid target includes a step of cycling the droplets thermally.

61. The method of paragraph 52, wherein the second signal is detected from a dye that is selectively localized near or at a perimeter of each droplet.

62. The method of paragraph 61, wherein the dye is selectively localized in, on, or about a skin that encapsulates droplets individually.

63. The method of paragraph 52, wherein the second signal is detected from a dye that is distributed at least substantially uniformly throughout each droplet.

64. The method of paragraph 52, wherein the step of determining a total number includes a step of counting each droplet of the plurality of droplets.

65. The method of paragraph 52, wherein the step of determining a total number includes a step of counting only a portion of the plurality of droplets and a step of estimating the total number based on the portion counted.

66. The method of paragraph 52, wherein the step of obtaining includes a step of determining a fraction of the droplets that are positive or a fraction that are negative for the target.

67. The method of paragraph 66, wherein the step of obtaining includes a step of finding a concentration of the target in the plurality of droplets based on a Poisson distribution of the target in the droplets.

VIII. Detection Systems

This Section describes exemplary detection systems, for example, for detecting sample-containing droplets. The systems may involve sensing or detecting the droplets themselves and/or contents of the droplets. The detection of droplets themselves may include determining the presence or absence of a droplet (or a plurality of droplets) and/or a characteristic(s) of the droplet, such as its size (e.g., radius or volume), shape, type, and/or aggregation state, among others. The detection of the contents of droplets may include determining the nature of the contents (e.g., whether or not the droplet contains a sample(s)) and/or a characteristic of the contents (e.g., whether or not the contents have undergone a reaction, such as PCR, the extent of any such reaction, etc.).

The detection of droplets and their contents, if both are detected, may be performed independently or coordinately, in any suitable order. For example, the detection may be performed serially (one droplet at a time), in parallel, in batch, and so forth.

The detection of droplets and their contents may be performed using any technique(s) or mechanism(s) capable of yielding, or being processed to yield, the desired information. These mechanisms may include optical techniques (e.g., absorbance, transmission, reflection, scattering, birefringence, dichroism, fluorescence, phosphorescence, etc.), electrical techniques (e.g., capacitance), and/or acoustic techniques (e.g., ultrasound), among others. The fluorescence techniques, in turn, may include fluorescence intensity, fluorescence polarization (or fluorescence anisotropy) (FP), fluorescence correlation spectroscopy (FCS), fluorescence recovery after photobleaching (FRAP), total internal reflection fluorescence (TIRF), fluorescence resonance energy transfer (FRET), fluorescence lifetime, and/or fluorescence imaging, among others.

The remainder of this Section describes exemplary detection systems, including droplet sensors and reaction sensors. In these exemplary systems, the droplet sensor may generate and detect scattered light, and the reaction sensor may generate and detect fluorescence, among other approaches. These systems are described, for convenience, in the context of a PCR reaction; however, the techniques apply more generally to any reaction, such as a biochemical reaction, capable of generating, or being modified to generate, a detectable signal.

In an exemplary PCR assay (or other nucleic acid amplification assay), the sample is first combined with reagents in a droplet, and the droplet is then thermocycled to induce PCR. It may then be desirable to measure the fluorescence of the droplets to determine which, if any, contained one or more target nucleotide sequences. This generally involves illuminating the droplets with radiation at a wavelength chosen to induce fluorescence, or a change in a characteristic of the fluorescence, from one or more fluorescent probes associated with the amplified PCR target sequence(s). For example, in an exemplary fluorescence intensity assay, if a relatively large intensity of fluorescence is detected, this indicates that PCR amplification of the target nucleotide occurred in the droplet, and thus that the target was present in that portion of the sample. Conversely, if no fluorescence or a relatively small intensity of fluorescence is detected, this indicates that PCR amplification of the target nucleotide did not occur in the droplet, and thus that a target was likely not present in that portion of the sample. In other fluorescence-based embodiments, the extent of reaction could be determined from a decrease in fluorescence intensity, instead of a decrease, and/or a change in one or more other fluorescence parameters, including polarization, energy transfer, and/or lifetime, among others.

A. Example 1

Detection System 1

This example describes an optical detection system based on measuring the end-point fluorescence signal of each sample/reagent droplet after a PCR amplification process is complete. The exemplary system is suitable for making both qualitative and quantitative measurements; see FIGS. 28 and 29.

Figure 28:
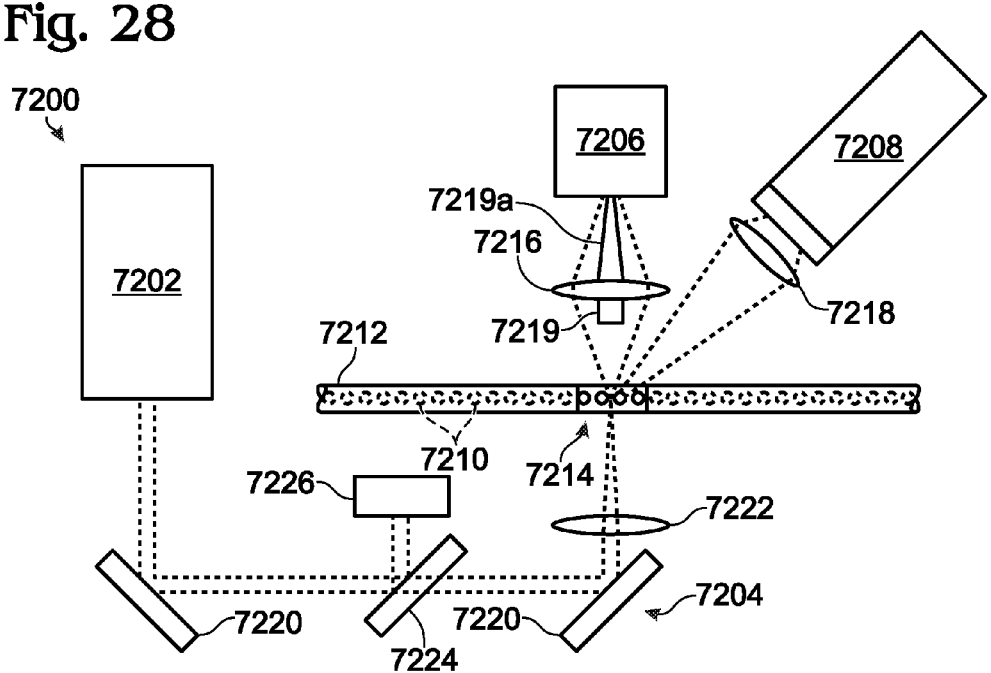
FIG. 28 is a schematic depiction of an optical detection system for irradiating sample-containing droplets and detecting fluorescence subsequently emitted by the droplets, in accordance with aspects of the present disclosure.

FIG. 28 depicts a cytometry-type optical detection system, generally indicated at 7200. The term "cytometry" refers to the fact that the detection system is configured to detect both scattered and fluorescence radiation. Detection system 7200 includes a radiation source 7202, transmission optics generally indicated at 7204, a forward scatter detector 7206, and a fluorescence detector 7208. The forward scatter detector may be replaced or augmented, in some embodiments, by side and/or back scatter detectors, among others, configured to detect light detected to the side or back of the sample, respectively. Similarly, the fluorescence detector may be replaced or augmented, in some embodiments, by an epi-fluorescence detector, among others, configured to detect fluorescence emitted anti-parallel to the excitation light (e.g., back toward transmission optics 7204 (which could, in such embodiments, include a dichroic or multi-dichroic beam splitter and suitable excitation and emission filters)).

Sample-containing droplets 7210, which have already undergone at least some degree of PCR thermocycling, are transferred through a capillary tube or other similar fluid channel 7212, which intersects the path of radiation from radiation source 7202 at an intersection region generally indicated at 7214. An optical element 7216, such as a converging lens, may be placed between intersection region 7214 and forward scatter detector 7206, to focus scattered radiation on the scatter detector. Similarly, an optical element 7218 may be placed between intersection region 7214 and fluorescence detector 7208, to focus fluorescence radiation on the fluorescence detector. The system may include an obscuration bar 7219, operatively positioned between the sample and detector, which reduces the amount of direct (unscattered) excitation radiation (light) that falls on the detector. The obscuration bar, shown here as a small square object in front of optical element 7216, may create a triangular-shaped shadow 7219a behind the optical element. This arrangement makes it easier for detector 7206 to detect changes in index of refraction that have scattered (at small angles) the normal beam.

Radiation from source 7202 may be partially scattered when it encounters a droplet, and the scattered radiation may be used to determine one or more properties of the droplet. For example, scattered radiation indicating the presence of a droplet in intersection region 7214 may be sensed by scatter detector 7206, and this information may be used to activate fluorescence detector 7208, which may otherwise remain deactivated (i.e., when a droplet is not present in the intersection region) to conserve power within the system. Even if the fluorescence detector remains continuously active, detecting the presence of a droplet may be useful for other purposes. For example, tracking the droplets passing through intersection region 7214 may be desirable because some droplets passing through the intersection region may not be detected by the fluorescence detector (e.g., if the droplets do not contain reaction product). In addition, tracking the droplets may allow background noise (i.e., the signal received by the detector in the absence of a droplet) to be removed, improving the signal-to-noise ratio. Furthermore, as described below, various properties of a detected droplet may be estimated from data sensed by forward or side scatter detector 7206.

Radiation detected by scatter detector 7206 may be used to infer the size (or other properties) of a detected droplet. Specifically, a measurement of the duration of a scattering event representing the presence of a droplet within intersection region 7214, in conjunction with knowledge of the average speed of droplet passage through the intersection region, can be used to determine the width of the droplet in a plane normal to the direction of the incident radiation from source 7202. If this width is less than the diameter of channel 7214, then it can be inferred that the droplet is an approximate sphere with a diameter less than the diameter of channel 7214, and the volume of the droplet can be calculated. If, on the other hand, the width of the droplet exceeds the diameter of channel 7214, this indicates that the droplet is likely contacting the walls of the channel and is not spherical. However, the droplet volume still may be estimated by modeling the droplet as a cylinder or other similar shape passing through the channel. As described below, a determination of droplet volume may be useful for normalizing the results of any corresponding fluorescence detection.

In some cases, radiation from source 7202 also may be scattered from intersection region 7214 even if it does not encounter a droplet, for instance, if it encounters a partially reflective surface such as a fluid interface or a wall of fluid channel 7212. This type of scattered radiation will generally have a different signature than radiation scattered from a droplet, so that it generally serves merely as a background for droplet scattering events. Whether scattering occurs in the absence of a droplet depends on the particular configuration of system 7200, as will be described below. Similarly, scattering may occur when droplets outside a desired size range pass through the intersection region, and the signature of radiation scattered from such droplets may be used to affect the subsequent treatment of such droplets. For example, the fluorescence signals received from unusually small or large droplets may be removed from a statistical sample, to increase statistical accuracy. In any case, after passing through intersection region 7214, scattered and/or unscattered radiation from radiation source 7202 is directed toward forward scatter detector 7206.

Radiation from source 7202 that is absorbed by droplets within intersection region 7214 may stimulate the emission of fluorescence radiation that can be detected by fluorescence detector 7208. More specifically, radiation intersecting a droplet may excite a fluorescent probe, such as a TAQMAN probe, that is configured to fluoresce significantly only if the fluorescent portion of the probe becomes separated from a quencher molecule. This separation, or cleaving, typically occurs only when polymerase replicates a sequence to which the probe is bound. In other words, a probe will fluoresce significantly only in droplets within which a target nucleotide sequence has been amplified through PCR. Accordingly, radiation source 7202 will generally be configured to emit radiation at a wavelength that stimulates fluorescent emission from one or more probes known to be present in the sample, and fluorescence detector 7208 will be configured to detect such stimulated radiation.

Radiation source 7202 may take any form suitable for transmitting radiation at one or more desired wavelengths or wavelength bands. For example, radiation source 7202 may be a laser, such as a diode laser, emitting substantially monochromatic light at a wavelength of 488 nanometers (nm) or at some other desired wavelength. Radiation source 7202 also may include multiple separate lasers, emitting light at either a single wavelength or at multiple different wavelengths. One or more (or all) of the lasers of radiation source 7202 may be replaced by an alternate source of light, such as a light-emitting diode (LED) configured to emit a directed beam of radiation at one or more desired wavelengths. In yet other embodiments, white light illumination, for example, from a Halogen lamp, may also be used to provide the radiation source.

Transmission optics 7204 may include any optical components suitable for directing, focusing, or otherwise desirably affecting radiation from source 7202. For example, as depicted in FIG. 28, the transmission optics may include one or more steering mirrors 7220, each configured to direct incident radiation in a desired direction such as toward another optical component or toward intersection region 7214. Also as depicted in FIG. 28, the transmission optics may include a converging lens 7222, which is configured to focus radiation from source 7202 onto intersection region 7214 to maximize scattering and fluorescence caused by the radiation. The transmission optics may further include additional components such as aperture stops, filters, diverging lenses, shaped mirrors, and the like, to affect the transmission path and/or properties of the radiation from source 7202 before it arrives at intersection region 7214. In addition, the transmission optics further may include (in this and other embodiments) a mechanism for monitoring properties of the incident (excitation) radiation. For example, the transmission optics may include a partial mirror 7224 for reflecting a portion of the incident radiation to a detector 7226, such as a photodiode, for monitoring the intensity of the incident light. This would allow correction of the detected scattering and fluorescence for changes that simply reflect changes in the intensity of the incident light.

Forward scatter detector 7206 is configured to receive and detect radiation scattered from droplets passing through intersection region 7214, as described previously. Various types of detectors may be suitable, depending on the desired cost and/or sensitivity of the detector. In approximate order of decreasing sensitivity, exemplary types of scatter detectors that may be suitable include photodiodes, avalanche photodiodes, multi-pixel photon counters, and photomultiplier tubes. The presence of optical element 7216, which typically will be a converging lens used to refocus scattered radiation toward scatter detector 7206, may decrease the necessary sensitivity of the forward scatter detector for a given application, by increasing the intensity per unit area of scattered radiation incident on the detector.

Fluorescence detector 7208 is configured to receive and detect fluorescence radiation emitted by droplets at or near the time they pass through intersection region 7214. Various types of fluorescence detectors may be suitable, depending on factors such as desired cost and/or sensitivity, including photodiodes, avalanche photodiodes, multi-pixel photon counters, and photomultiplier tubes. Also as in the case of the forward scatter, utilizing an optical element 7218, typically a converging lens, between intersection region 7214 and fluorescence detector 7208 may decrease the necessary sensitivity of the fluorescence detector by increasing the intensity per unit area of fluorescence radiation incident on the detector.

Figure 29:
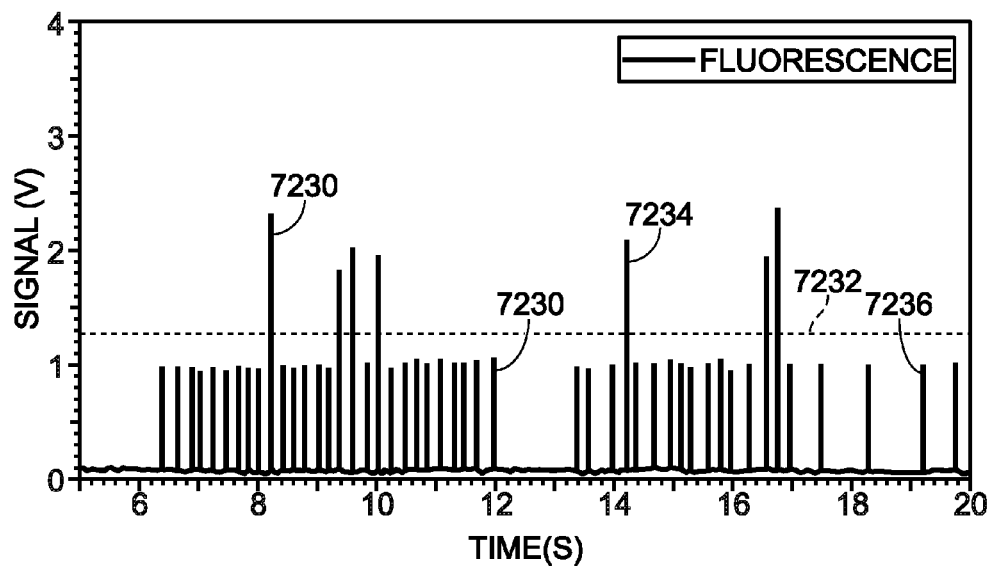
FIG. 29 is a graph of intensity versus time for fluorescence detected by an optical detection system such as the system of FIG. 28, illustrating the distinction between fluorescence emitted by droplets containing a target and droplets not containing a target.

FIG. 29 depicts exemplary fluorescence measurements made by fluorescence detector 7208. More specifically, FIG. 29 shows a post-PCR end-point fluorescence trace from droplets, in which each "peak" 7230 represents the intensity of detected fluorescence emitted by an individual droplet flowing through intersection region 7214. As FIG. 29 indicates, the resulting histogram can be used to identify positive from negative signals. Specifically, the signals depicted in FIG. 29 each may be compared to a cut-off or threshold fluorescence level, as indicated by dashed line 7232. Signals exceeding the threshold level will be interpreted as positive for PCR amplification, and thus for the presence of the target nucleotide sequence in the corresponding droplet, as indicated for an exemplary signal at 7234. On the other hand, signals falling below threshold level 7232 will be interpreted as negative outcomes, indicating that the corresponding droplet did not contain the target.

An example of a negative signal is indicated at 7236, where the detection of a sub-threshold amount of fluorescence is due to the presence of uncleaved fluorescent probe in the droplet. As described previously, the fluorescence of such probes is generally not completely quenched even in the absence of cleavage by a binding polymerase. Also, the differences in fluorescent intensity of a positive, as seen in the signal voltage peak heights between the positive peak at 7230 and positive peak 7234, can be attributed to different amounts of starting nucleic acid target originally in the droplet prior to PCR (e.g., one versus two starting targets). The ratio of different amounts of starting target amounts may be governed by Poisson statistics.

Typically, hundreds to millions of droplets are analyzed per run. In any case, after a desired number of signals have been detected by fluorescence detector 7208, i.e., after a desired number of droplets have passed through intersection region 7214, the positive and negative signals are counted and analyzed. Analysis is typically performed using receiver-operator characteristic curves and Poisson statistics to determine target presence and target concentration, respectively. Running analysis using Poisson statistics can also be performed to give an estimate of target concentration prior to processing all the droplets (i.e., subsets of the total droplets are used in the statistical analysis). The analysis of droplets is further described in Section VII.

B. Example 2

Detection Methods

Figure 30:
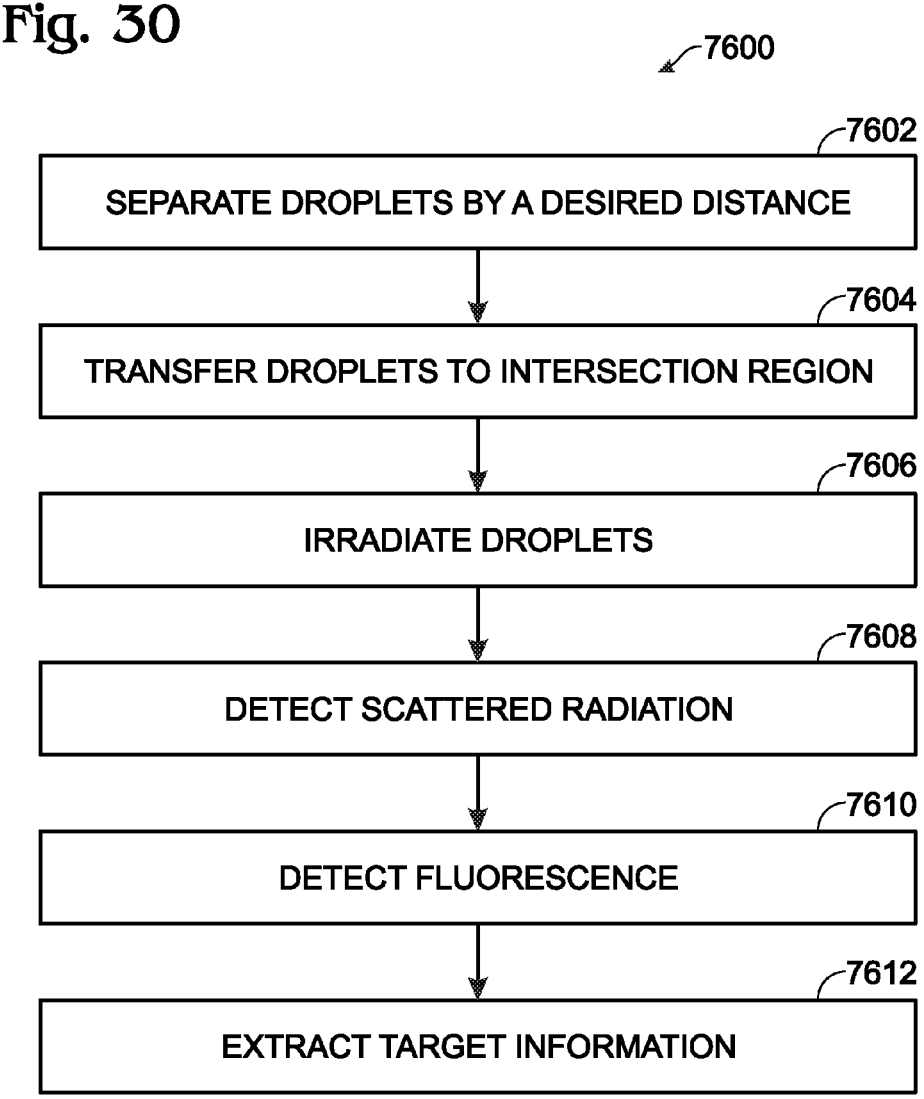
FIG. 30 is a flow chart depicting a method of detecting fluorescence from sample-containing droplets, in accordance with aspects of the present disclosure.

This example describes a method of detecting fluorescence from sample-containing droplets that have undergone PCR thermocycling; see FIG. 30.

FIG. 30 is a flowchart depicting the steps of a fluorescence detection method, generally indicated at 7600, which may be performed in conjunction with a PCR system of DNA amplification according to the present disclosure. Although various steps of method 7600 are described below and depicted in FIG. 30, the steps need not necessarily all be performed, and in some cases may be performed in a different order than the order shown in FIG. 30.

At step 7602, sample-containing droplets are separated by a desired average distance. This may be accomplished, for example, by various flow focusing techniques such as those described above (i.e., by flow focusing the droplets as they are generated), and/or by generating droplets at a suitable rate. In cases of batch detection such as in a stop-flow system, it may be appropriate for droplets to remain closely spaced during fluorescence detection, and accordingly a droplet separation step may not be performed.

At step 7604, the sample-containing droplets are transferred into a radiation intersection region, within which they will be exposed to illuminating radiation chosen to stimulate emission of fluorescence radiation from one or more fluorescent probes within the droplets, with an intensity that depends in part on whether or not a quenching moiety has been cleaved from the probe due to polymerase binding of the associated nucleotide target primer. In the case of continuous flow detection, the intersection region may be disposed within a fluid channel such as a capillary tube. In the case of batch detection, the intersection region may be disposed within one or more detection chambers. In this case, transferring droplets into the intersection region may include steps such as opening and closing one or more valves to allow a continuous flow of droplets into and out of the intersection region.

At step 7606, the droplets in the radiation intersection region encounter and are irradiated with stimulating radiation, which includes at least one wavelength chosen to excite the fluorescent probe(s) known to be present in the reagents within the droplets. As described above, the illuminating radiation may be produced by a laser, and LED, or any other suitable radiation source, and may be transferred to the intersection region through free space or through one or more optical fibers. Furthermore, the radiation may be focused, diverged, split, filtered, and/or otherwise processed before reaching the intersection region, to efficiently irradiate the droplets in the most suitable manner for a particular detector system configuration.

At step 7608, radiation scattered from the droplets in the intersection region may be detected by a forward scattering detector. This step will typically not be performed in a batch detection system, where each droplet is approximately stationary or at least relatively slow moving in a detection chamber that serves as the radiation intersection region. However, detecting scattered radiation in a continuous flow detection system may help to correlate simultaneous or subsequent fluorescence detection with the presence of droplets in the intersection region, and may allow the volume and target molecule concentration of each droplet to be estimated, as described above. More generally, step 7608 may include performing any measurement to enable an estimation of the volume of each droplet, such as the amount of radiation scattered from the droplet, the time of flight of the droplet as it passes through the intersection region, an electrical property of the droplet, or a thermal property of the droplet. Method 7600 also may include estimating the volume of each droplet based on the measurement performed in step 7608.

At step 7610, fluorescence emitted by droplets irradiated in the intersection region is detected by a fluorescence detector. As described in the preceding examples, the emitted radiation may be transferred to the fluorescence detector with or without passing through one or more intermediate optical elements such as lenses, apertures, filters, or the like. The emitted radiation also may or may not be transferred to the fluorescence detector through one or more optical fibers. In batch detection applications, the detector and/or the intersection region may be configured to move in a manner that allows an optical scan of the intersection region by a detector having a smaller field of view than the entire intersection region.

At step 7612, detected fluorescence is analyzed to determine whether or not a particular target nucleotide sequence was present in the droplets. Additional information, including but not limited to an estimate of the number or fraction of droplets containing a target molecule, the average concentration of target molecules in the droplets, an error margin, and/or a statistical confidence level, also may be extracted from the collected data.

Using the data collected from each droplet in an analysis may be conditional and may depend, for example, on whether the estimated volume of the droplet falls within a particular predetermined range. More specifically, if the estimated volume of a droplet falls within a predetermined range, then the fluorescence intensity emitted by that droplet may be used in a determination of target molecule concentration in the sample, whereas if the estimated volume of the droplet falls outside the predetermined range, then the fluorescence intensity emitted by the droplet may be excluded from a determination of target molecule concentration in the sample.

C. Example 3

Additional Embodiments

This example describes additional aspects of sample detection, in accordance with aspects of the present disclosure, presented without limitation as a series of numbered sentences.

1. A method of detecting target molecule concentration in a sample, comprising (A) generating sample-containing droplets with a droplet generator; (B) amplifying target molecules within the droplets; (C) transferring the droplets through an intersection region where the droplets encounter radiation from a radiation source; (D) estimating the volume of each droplet based on a measurement performed as the droplet passes through the intersection region; (E) detecting fluorescence intensity emitted by each droplet; and (F) for each droplet, if the estimated volume of the droplet falls within a predetermined range then using the fluorescence intensity emitted by the droplet in a determination of target molecule concentration in the sample, and if the estimated volume of the droplet falls outside the predetermined range then excluding the fluorescence intensity emitted by the droplet from a determination of target molecule concentration in the sample.

2. The method of paragraph 1, wherein the measurement is an amount of radiation scattered from the droplet.

3. The method of paragraph 1, wherein the measurement is time of passage of the droplet through a detector field of view.

4. The method of paragraph 1, wherein the measurement is an electrical property of the droplet.

5. The method of paragraph 1, wherein the measurement is a thermal property of the droplet.

6. The method of paragraph 1, further comprising separating the droplets by a desired average distance prior to transferring them through the intersection region.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of performing a droplet-based assay, comprising:
    forming droplets from a same mixture, wherein only a subset of the droplets contain a target;
    irradiating a region of a channel;
    detecting a forward scattering signal and a fluorescence signal from a plurality of the droplets as each droplet passes through the region of the channel, wherein the fluorescence signal is detected from a label present in each droplet and varies according to whether the target is present in the droplet;
    identifying accepted droplets of the plurality for which the forward scattering signal meets a condition and rejected droplets of the plurality for which the forward scattering signal does not meet the condition, wherein the condition corresponds to a permitted size of a droplet; and
    determining a concentration of the target based on the fluorescence signal from the accepted droplets, and without any contribution of the fluorescence signal from the rejected droplets.

2. The method of claim 1, wherein the forward scattering signal has an intensity that is at least substantially independent of whether or not the target is present in the droplet.

3. The method of claim 1, wherein the forward scattering signal detected from each droplet forms a peak, and wherein the condition corresponds to a permitted width of the peak.

4. The method of claim 1, wherein the step of determining includes a step of determining a fraction of the accepted droplets that are positive or a fraction that are negative for the target.

5. The method of claim 1, wherein the forward scattering signal is produced by refraction of incident radiation.

* * * * *